US012685451B2

(12) United States Patent
McGoff

(10) Patent No.: US 12,685,451 B2
(45) Date of Patent: Jul. 21, 2026

(54) SYSTEMS, DEVICES, AND METHODS FOR GUIDING RESONANCE BREATHING VIA BIOFEEDBACK

(71) Applicant: Ohm Health, Inc., Richmond, VA (US)

(72) Inventor: James McGoff, Richmond, VA (US)

(73) Assignee: Ohm Health, Inc., Richmond, VA (US)

( * ) Notice: Subject to any disclaimer, the term of this patent is extended or adjusted under 35 U.S.C. 154(b) by 0 days.

(21) Appl. No.: 19/040,595

(22) Filed: Jan. 29, 2025

(65) Prior Publication Data

US 2025/0241546 A1 Jul. 31, 2025

Related U.S. Application Data

(60) Provisional application No. 63/733,349, filed on Dec. 12, 2024, provisional application No. 63/685,737, filed on Aug. 22, 2024, provisional application No. 63/626,915, filed on Jan. 30, 2024.

(51) Int. Cl.
| | |
|---|---|
| *A61B 5/024* | (2006.01) |
| *A61B 5/00* | (2006.01) |
| *A61B 5/113* | (2006.01) |

(52) U.S. Cl.
CPC ........ *A61B 5/02405* (2013.01); *A61B 5/1135* (2013.01); *A61B 5/7405* (2013.01); *A61B 5/7435* (2013.01)

(58) Field of Classification Search
CPC . A61B 5/02405; A61B 5/1135; A61B 5/7405; A61B 5/7435
See application file for complete search history.

(56) References Cited

U.S. PATENT DOCUMENTS

| | | | | |
|---|---|---|---|---|
| 5,267,566 A | * | 12/1993 | Choucair | ............. A61B 5/6838 600/493 |
| 2007/0299354 A1 | * | 12/2007 | Striepe | ............... A61B 5/02405 600/509 |
| 2010/0240945 A1 | | 9/2010 | Bikko | |
| 2013/0110264 A1 | * | 5/2013 | Weast | .................... H04B 1/385 700/91 |

(Continued)

OTHER PUBLICATIONS

International Search Report mailed May 5, 2025 for Application No. PCT/US2025/013608.

*Primary Examiner* — Amanda L Steinberg
(74) *Attorney, Agent, or Firm* — TROUTMAN PEPPER LOCKE LLP; Christopher J. Forstner; Scott A. Bergeson

(57) ABSTRACT

A system for guiding a user with heart rate variability feedback may include a computing device comprising a heart rate sensor, one or more processors, and memory having stored thereon computer program code that, when executed by the one or more processors, is configured to cause the one or more processors to receive user input, responsive to receiving the user input, cause an audio output device to output an audio content associated with a default breathing pattern, dynamically receive interbeat interval data from the heart rate sensor, dynamically extract one or more characteristics from the interbeat interval data, cause the display to indicate a dynamic visual pattern based on the one or more characteristics, dynamically determine a second breathing pattern based on the one or more characteristics, and dynamically cause the audio content to change based on the second breathing pattern.

30 Claims, 20 Drawing Sheets

(56)        References Cited

U.S. PATENT DOCUMENTS

| | | | |
|---|---|---|---|
| 2013/0171599 A1* | 7/2013 | Bleich | A63B 24/0062 |
| | | | 434/247 |
| 2016/0058376 A1* | 3/2016 | Baek | A61B 5/0205 |
| | | | 340/870.07 |
| 2017/0089782 A1* | 3/2017 | Hirt | A61B 5/681 |
| 2018/0056029 A1 | 3/2018 | Akimoto | |
| 2018/0256074 A1* | 9/2018 | Persidsky | A61B 5/113 |
| 2019/0038180 A1* | 2/2019 | Tzvieli | G02B 7/002 |
| 2021/0015446 A1* | 1/2021 | Ritchie | A61B 5/021 |
| 2021/0338971 A1* | 11/2021 | Blahnik | G06F 3/01 |
| 2022/0015653 A1* | 1/2022 | Persen | A61B 5/02405 |
| 2022/0071535 A1* | 3/2022 | Jernigan | A61B 5/0205 |
| 2024/0194344 A1* | 6/2024 | Capodilupo | A61B 5/7267 |
| 2024/0252051 A1* | 8/2024 | Khare | A61B 5/7264 |
| 2024/0315641 A1* | 9/2024 | Le | A61B 5/726 |

* cited by examiner 107a
104

107b
104

400c

DYNAMICALLY RECEIVE INTERBEAT INTERVAL DATA FROM HEART RATE SENSOR — 429

DYNAMICALLY TRANSMIT THE INTERBEAT INTERVAL DATA TO A BASE COMPUTING DEVICE — 430

DYNAMICALLY RECEIVE HAPTIC PATTERN DATA FROM THE BASE COMPUTING DEVICE — 432

CAUSE THE HAPTIC FEEDBACK DEVICE TO GENERATE A DYNAMIC HAPTIC PATTERN BASED ON THE HAPTIC PATTERN DATA — 434

200d

229

DYNAMICALLY RECEIVE INTERBEAT INTERVAL DATA FROM THE HEART RATE SENSOR

236

DYNAMICALLY DETERMINE A DYNAMIC HAPTIC PATTERN

234

CAUSE THE HAPTIC FEEDBACK DEVICE TO GENERATE THE DYNAMIC HAPTIC PATTEN

SYSTEMS, DEVICES, AND METHODS FOR GUIDING RESONANCE BREATHING VIA BIOFEEDBACK

CROSS REFERENCE TO RELATED APPLICATION

The patent application claims the benefit and priority claims priority under 35 U.S.C. § 119(e) to U.S. Provisional Patent Application No. 63/626,915, filed with the U.S. Patent and Trademark Office on Jan. 30, 2024, entitled Systems, Devices, and Methods for Guiding Resonance Breathing via Biofeedback, U.S. Provisional Patent Application No. 63/685,737, filed with the U.S. Patent and Trademark Office on Aug. 22, 2024, entitled Systems, Devices, and Methods for Guiding Resonance Breathing via Biofeedback, and U.S. Provisional Patent Application No. 63/733,349, filed with the U.S. Patent and Trademark Office on Dec. 12, 2024, entitled Systems, Devices, and Methods for Guiding Resonance Breathing via Biofeedback, the disclosure of each of which is incorporated by reference herein in its entirety as part of the present application.

FIELD

The disclosed technology relates to systems, devices, and methods for guiding resonance breathing via biofeedback.

BACKGROUND

The United States is experiencing a mental health crisis. A large number of adults are stressed to the point that they cannot function, and a majority of Americans believe that it is harder to find a mental health care provider that it is a physical health care provider. While meditation, mental health apps, talk therapy, and pharmaceuticals may provide some relief for stress or anxiety, they are difficult to use or access, time consuming, or require medication that may include side effects. In addition, these methods do not provide a clear and direct method for improving a person's nervous system adaptability.

Accordingly, there is a need for improved systems, devices, and methods for dynamically guiding a user to effectively conduct resonance breathing using biofeedback (e.g., heart rate variability feedback). Put another way, there is a need for systems, devices, and methods to deliver an evidence-based biofeedback protocol at-home experience that is drug-free, screen-free, intuitive, immediately accessible, and improve a person's nervous system adaptability to stress and anxiety. Embodiments of the present disclosure may be directed to this and other considerations.

SUMMARY

A system for efficiently guiding resonance breathing using biofeedback (e.g., heart rate variability feedback).

In an aspect, a system for dynamically guiding a user with heart rate variability feedback, the system including a first computing device comprising an audio output device (e.g., one or more speakers) and a display (e.g., one or more lights). The system also including a second computing device comprising a heart rate sensor, one or more processors, and memory having stored thereon computer program code that, when executed by the one or more processors, is configured to cause the one or more processors to perform certain method steps. Those method steps include receiving user input, responsive to receiving the user input, causing the audio output device to output an audio content associated with a default breathing pattern, dynamically receiving interbeat interval data from the heart rate sensor, dynamically extracting one or more characteristics from the interbeat interval data, causing the display to indicate a dynamic visual pattern based on the one or more characteristics, dynamically determining a second breathing pattern based on the one or more characteristics, and dynamically causing the audio content to change based on the second breathing pattern.

In an aspect, a computing device including one or more processors and a memory having stored thereon computer program code that, when executed by the one or more processors, is configured to cause the one or more processors to perform certain method steps. Those method steps include dynamically receiving interbeat interval data from an instantaneous heart rate sensor, where the interbeat interval data comprises one or more interbeat intervals, causing an audio output device to output an audio content associated with a default breathing pattern, dynamically extracting one or more characteristics from the interbeat interval data in real time, dynamically determine a second breathing pattern based on the one or more characteristics, and cause the audio content to dynamically change based on the second breathing pattern.

In an aspect, a system includes a first computing device. The first (e.g., base) computing device includes a display (e.g., one or more lights) and an audio output device (e.g., one or more speakers). The system also includes a second (e.g., remote) computing device. The second computing device may include an instantaneous heart rate sensor, one or more processors, and a memory having stored thereon computer program code that, when executed by the one or more processors, is configured to cause the one or more processors to perform certain method steps. These method steps include dynamically receiving interbeat interval data from the instantaneous heart rate sensor, wherein the interbeat interval data comprises one or more interbeat intervals, dynamically extracting one or more characteristics from the interbeat interval data; and causing the display (e.g., one or more lights) to indicate a dynamic heart rate variability pattern based on the one or more characteristics.

In an aspect, a system for dynamically guiding resonance breathing based on biofeedback. The system may include a first computing device. The first computing device may include a heart rate sensor. The system may include a second computing device. The second computing device may include an audio output device, a display, one or more processors, and a memory. The memory may have stored thereon computer program code that, when executed by the one or more processors, may be configured to cause the one or more processors to perform a method. The method may include receiving user input via the first computing device or the second computing device, responsive to receiving the user input, outputting an audio content associated with a default breathing pattern via the audio output device, dynamically receive receiving interbeat interval data from the heart rate sensor, dynamically extracting one or more characteristics from the interbeat interval data, causing the display to indicate a dynamic visual pattern based on the one or more characteristics, dynamically determining a second breathing pattern based on the one or more characteristics; and dynamically changing the audio pattern based on the second breathing pattern.

In an aspect, a base computing device may include one or more processors; and a memory having stored thereon computer program code that, when executed by the one or more processors, may be configured to cause the one or more processors to execute a method. The method may include dynamically receiving interbeat interval data from an instantaneous heart rate sensor. The interbeat interval data may include one or more interbeat intervals. The method may also include outputting an audio content associated with a default breathing pattern via an audio output device, dynamically extracting one or more characteristics from the interbeat interval data in real time, dynamically determining a second breathing pattern based on the on the one or more characteristics, and dynamically changing the audio content based on the second breathing pattern.

In an aspect, a base computing device, may include one or more processors and a memory having stored thereon computer program code that, when executed by the one or more processors, may be configured to cause the one or more processors to perform a method. The method may include dynamically receiving interbeat interval data from an instantaneous heart rate sensor. The method may also include dynamically extracting one or more characteristics from the interbeat interval data and causing a display to indicate a dynamic heart rate variability pattern based on the one or more characteristics. The interbeat interval data may include one or more interbeat intervals.

In an aspect, a user input device may include a heart rate sensor, a haptic feedback device, a transceiver, one or more processors, and a memory having stored thereon computer program code that, when executed by the one or more processors, may be configured to cause the one or more processors to perform a method. The method may include dynamically receiving interbeat interval data from the heart rate sensor. The method may include dynamically transmitting, via the transceiver over a wireless connection, the interbeat interval data to a base computing device, dynamically receiving, via the transceiver over the wireless connection, haptic pattern data from the base computing device, and causing the haptic feedback device to generate a dynamic haptic pattern based on the haptic pattern data. The interbeat interval data may include one or more interbeat intervals.

In an aspect, a user input device may include a heart rate sensor, a haptic feedback device, a transceiver, one or more processors, and a memory having stored thereon computer program code that, when executed by the one or more processors, may be configured to cause the one or more processors to perform a method. The method may include dynamically receiving interbeat interval data from the heart rate sensor. The method may also include dynamically determining a dynamic haptic pattern and causing the haptic feedback device to generate the dynamic haptic pattern. The interbeat interval data may include one or more interbeat intervals.

In an aspect, a base computing device may include an audio output device, a display, a transceiver, one or more processors, and a memory having stored thereon computer program code that, when executed by the one or more processors, may be configured to cause the one or more processors to perform a method. The method may include receiving, the transceiver over a wireless connection, interbeat interval data from a user input device, responsive to receiving, via the transceiver over the wireless connection, the interbeat interval data or receiving user input, outputting an audio pattern associated with a default breathing pattern from the audio output device; dynamically extract one or more characteristics from the interbeat interval data, causing the display to indicate a heart rate variability pattern based on the one or more characteristics, dynamically determining a second breathing pattern based on the one or more characteristics, and dynamically changing the audio pattern based on the second breathing pattern. The interbeat interval data may include one or more interbeat intervals and the user input device may include an instantaneous hear rate sensor.

In an aspect, a system for dynamically guiding resonance breathing based on biofeedback. The system may include a first computing device, which may include a heart rate sensor, a haptic feedback device, and a first transceiver. The system may include a base computing device, which may include an audio output device, a display, a second transceiver, one or more processors, and a memory having stored thereon computer program code that, when executed by the one or more processors, is configured to cause the one or more processors to perform a method. The method may include receiving, from the heart rate sensor via a wireless connection between the first transceiver and the second transceiver, interbeat interval data from the heart rate sensor, responsive to receiving the interbeat interval data or user input, outputting an audio pattern associated with a default breathing pattern on the audio output device, dynamically extracting one or more characteristics from the interbeat interval data, causing the display to indicate a heart rate variability pattern based on the one or more characteristics, dynamically determining a second breathing pattern based on the one or more characteristics, and dynamically changing the audio pattern based on the second breathing pattern. The interbeat interval data may include one or more interbeat intervals.

In an aspect, a system for dynamically guiding resonance breathing based on biofeedback. The system may include a first computing device, which may include a heart rate sensor. The system may also include a second computing device, which may include a display, one or more processors; and a memory having stored thereon computer program code that, when executed by the one or more processors, may be configured to cause the one or more processors to perform a method. The method may include dynamically receive interbeat interval data from the heart rate sensor, responsive to receiving user input via the first computing device, outputting a display pattern associated with a default breathing pattern via the display, dynamically extracting one or more characteristics from the interbeat interval data, dynamically determining a second breathing pattern based on the one or more characteristics, and dynamically changing the display pattern based on the second breathing pattern. The interbeat interval data may include one or more interbeat intervals.

Further implementations, features, and aspects of the disclosed technology, and the advantages offered thereby, are described in greater detail hereinafter, and can be understood with reference to the following detailed description, accompanying drawings, and claims.

BRIEF DESCRIPTION OF THE DRAWINGS

Reference will now be made to the accompanying drawings, which are not necessarily drawn to scale, and which illustrate various implementations, aspects, and principles of the disclosed technology. In the drawings.

DETAILED DESCRIPTION

Figure 1A:
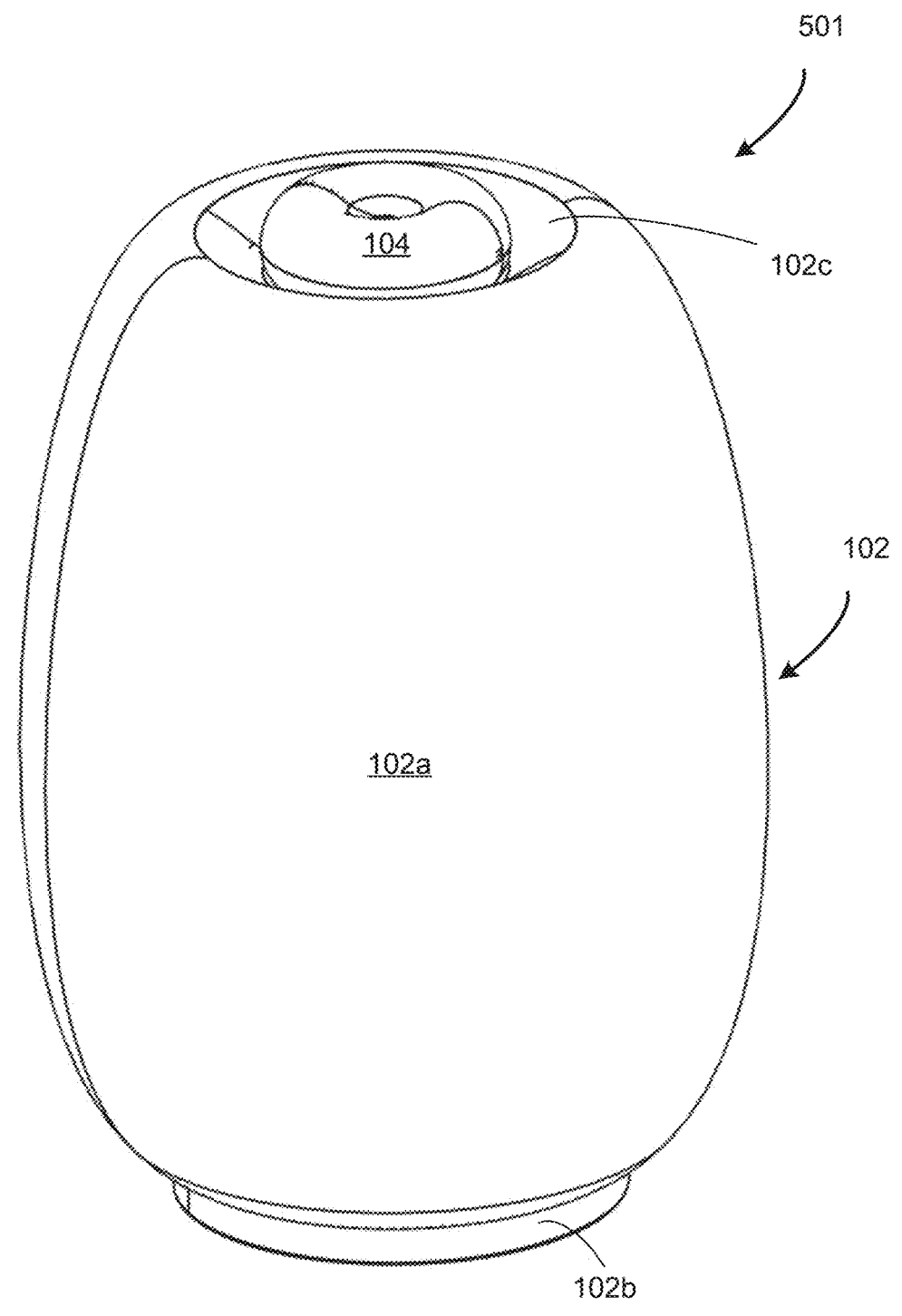
FIG. 1A is an upper perspective view of a biofeedback system, in accordance with certain embodiments of the disclosed technology.

Systems, devices, and methods for guiding resonance breathing are disclosed herein. In some examples, this technology advantageously allows a user to use a dynamic and customized biofeedback (e.g., heart rate variability biofeedback) to quickly achieve resonance breathing and maintain breathing in such as way the user is able to conduct resonance breathing as long as desired.

The resonance breathing pattern can be characterized as a smooth, sinusoidal pattern of changes in instantaneous heart rate over time. In other words, a smooth heart rate variability curve is an emergent property of the fact that the most influential incoming superimposed signals to the heart correspond to similar frequencies. The resonance breathing pattern may correspond to the presence and predominance of low frequency power as a ratio to all power including low frequency, high frequency, and very low frequency. The resonance breathing pattern may also correspond to exaggerated peak to trough amplitudes (think two people jumping on a trampoline—they bounce higher and lower if they are jumping at the same rate). The resonance breathing pattern may be associated with a higher root mean square of successive difference between normal heartbeats (rMSSD) value than initial or normal rMSSD values. Put another way, if a person's peak-trough amplitude is consistently 2-4 times a typical peak-trough amplitude, it may indicate the presence of resonance between the baroreceptor reflex and the respiratory sinus arrhythmia. Higher peak-trough amplitudes are associated with improved heart rate variability, a more resilient nervous system, higher vagal tone, and healthier stress response. Over time, a user of the technology described and illustrated herein may improve their vagal tone more quickly than traditional methods or other devices.

In some aspects described above and below, pulse wave characteristic data may be used in place of or in addition to interbeat interval data. Pulse wave characteristics may include a measurement of blood volume changes in a user's arteries, which correspond to each heartbeat. These measurements are typically captured using one or more photoplethysmography (PPG) sensors. The pulse wave characteristic data can be analyzed to detect the time points of successive heartbeats (often called pulse peaks (e.g., pulse wave systolic peak and pulse wave diastolic peak) or troughs (e.g., a dicrotic notch and a beginning and an end of a pulse wave)). The time interval between these points is referred to as the interbeat interval (or pulse propagation time). By measuring the time between these peaks, the one or more computing devices described herein may calculate the interbeat interval.

Some implementations of the disclosed technology will be described more fully with reference to the accompanying drawings. This disclosed technology may, however, be embodied in many different forms and should not be construed as limited to the implementations set forth by way of the examples herein. The components described hereinafter as making up various elements of the disclosed technology are intended to be illustrative and not restrictive. Many suitable components that would perform the same or similar functions as components described herein are intended to be embraced within the scope of the disclosed electronic devices, systems, and methods.

Reference will now be made in detail to example embodiments of the disclosed technology that are illustrated in the accompanying drawings and disclosed herein. Wherever convenient, the same reference numbers will be used throughout the drawings to refer to the same or like parts.

FIGS. 1A-1F illustrate a biofeedback system 701 that is configured to guide a user to quickly achieve and maintain resonance breathing for a desired period. As will be described in more detail, when a user initiates a breathing session with biofeedback system 701, biofeedback system 701 outputs audio feedback, haptic feedback, and/or visual feedback to guide a user to quickly arrive at a resonance state between the baroreceptor reflex and the respiratory sinus arrhythmia. Initially, the biofeedback system 701 provides this feedback in a default pattern, which biofeedback system 701 may select from a number of default patterns, based on certain physiological data (e.g., historical interbeat interval data and/or blood pressure data). As biofeedback system 701 collects and analyzes physiological data (e.g., interbeat interval data), biofeedback system 701 dynamically determines or generates updated breathing patterns, which in turns outputs updated audio feedback, haptic feedback, and/or visual feedback to help a user reach resonance state quickly.

Figure 1B:
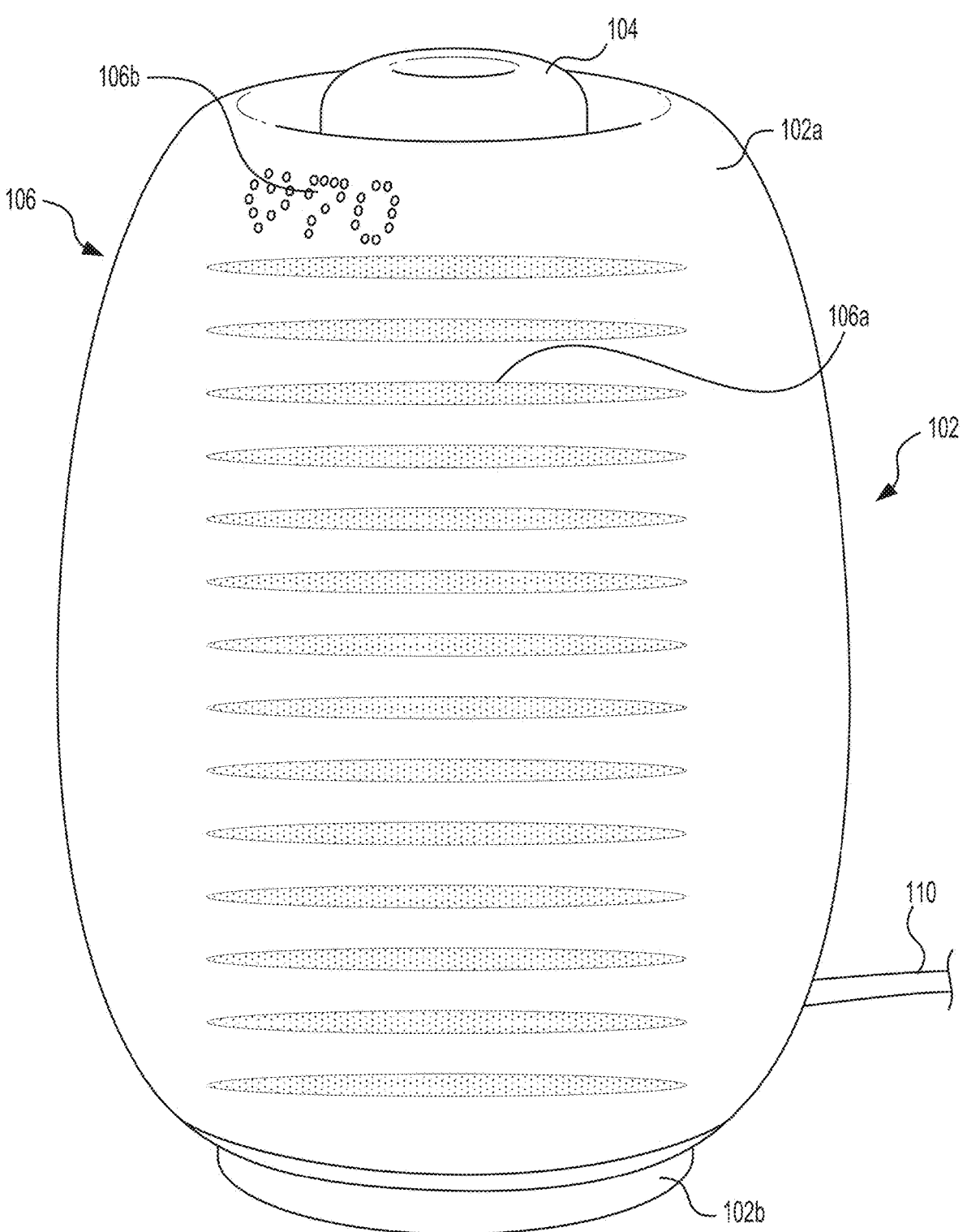
FIG. 1B is a schematic image of the biofeedback system, in accordance with certain embodiments of the disclosed technology.
Figure 1C:
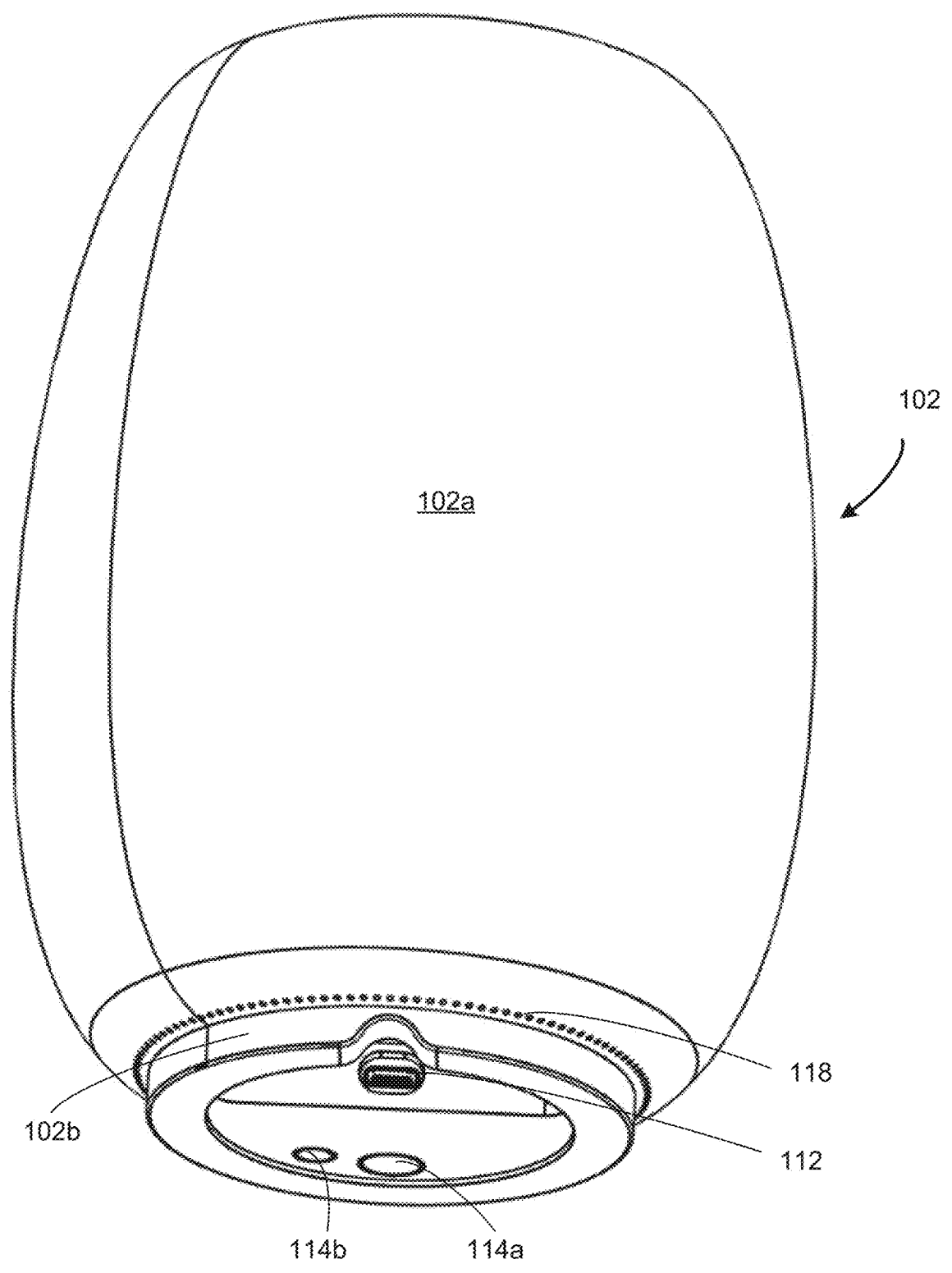
FIG. 1C is a lower perspective view of the biofeedback system, in accordance with certain embodiments of the disclosed technology.
Figure 1D:
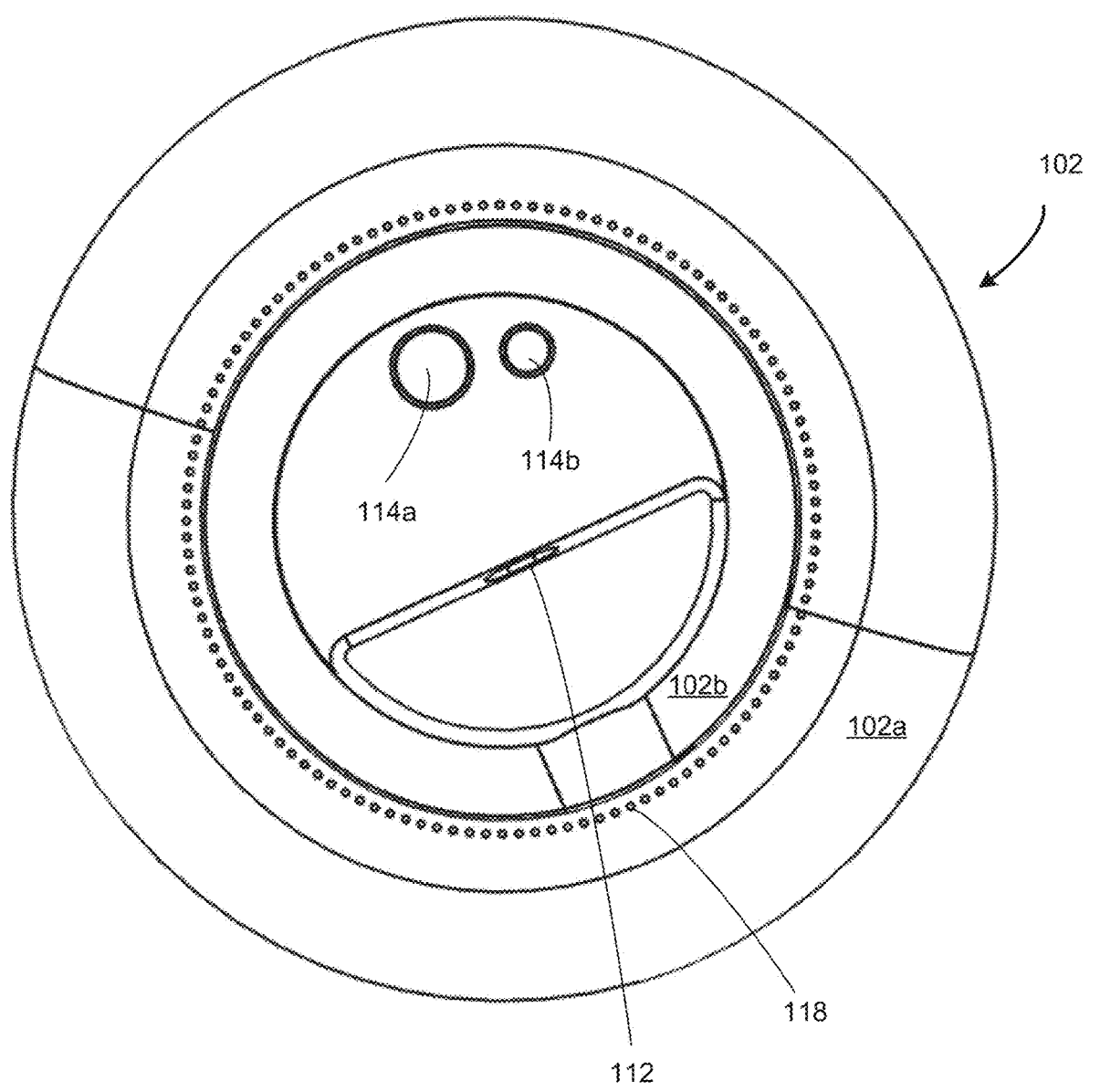
FIG. 1D is a bottom view of the biofeedback system, in accordance with certain embodiments of the disclosed technology.
Figure 1E:
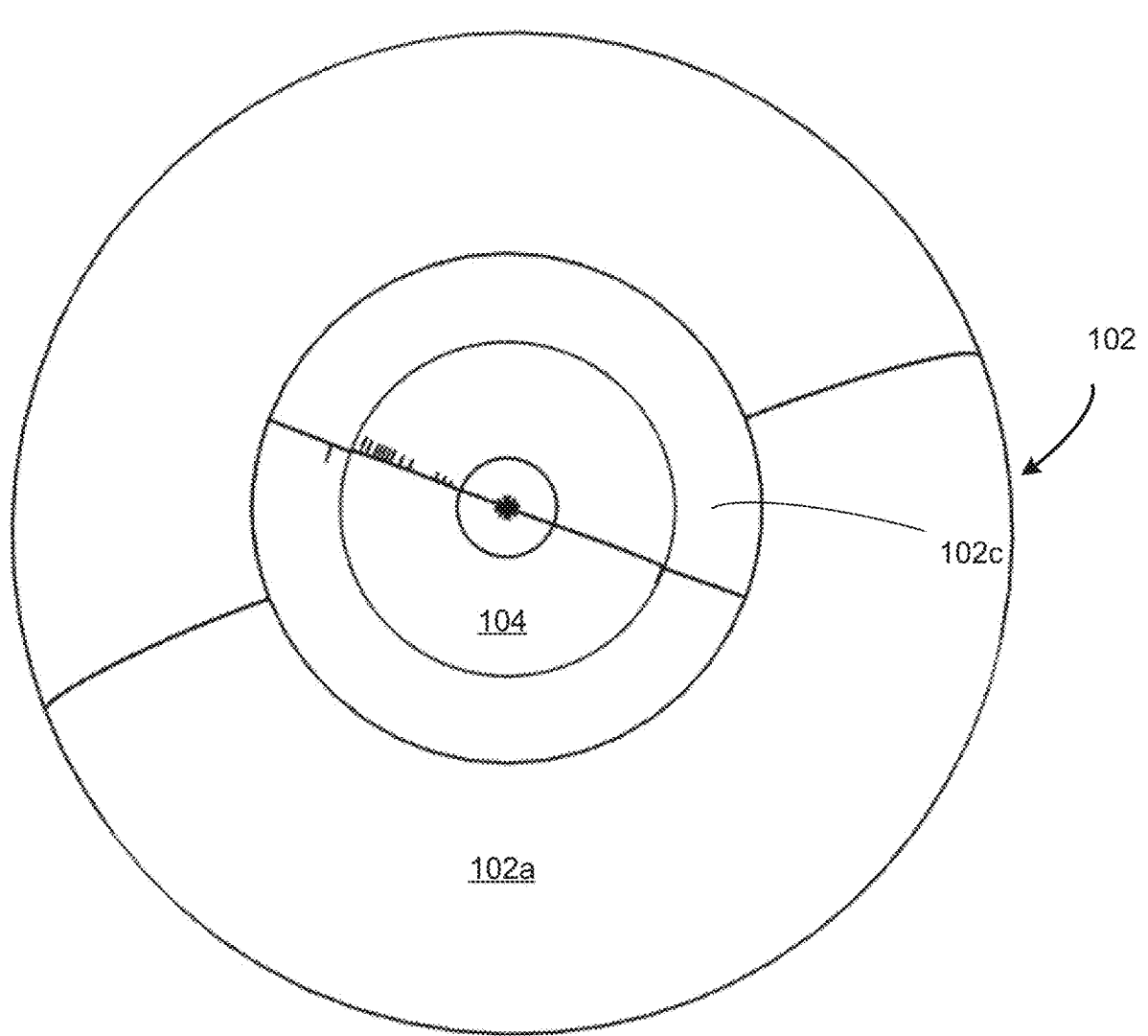
FIG. 1E is a top view of the biofeedback system, in accordance with certain embodiments of the disclosed technology.
Figure 1F:
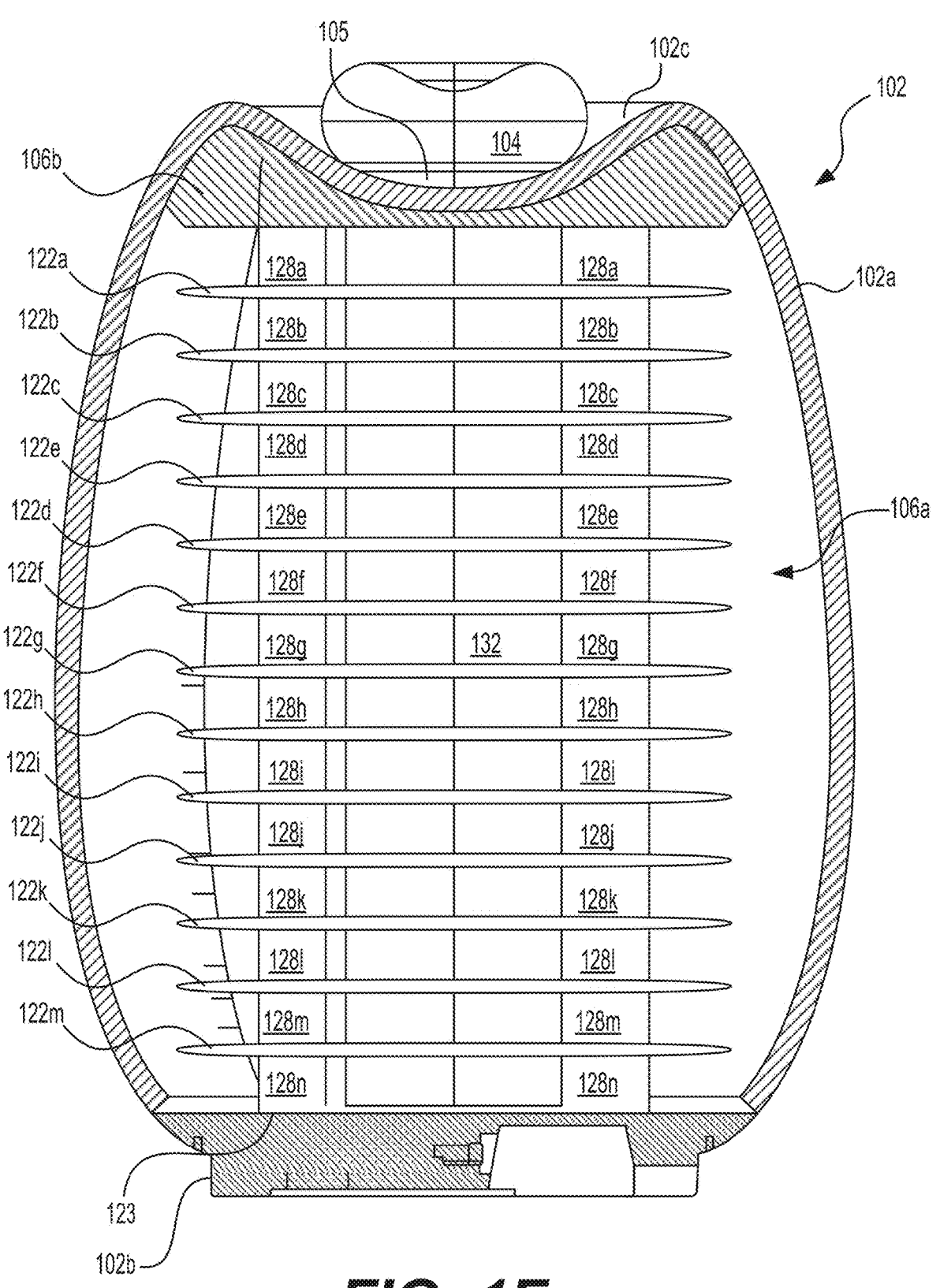
FIG. 1F is a cutaway side view of the biofeedback system, in accordance with certain embodiments of the disclosed technology.

As shown in FIGS. 1A and 1E, biofeedback system 701 may include a first or base computing device 102 and a second (e.g., remote) computing device 104. Base computing device 102 may include an upper portion 102a and a lower portion 102b. Upper portion 102a may include a cradle 102c configured to receive and hold the second computing device 104. Cradle 102c may include an upper surface that comprises a concave shape. As shown in FIG. 1F, cradle 102c may include one or more induction charging coils 105 configured to charge the second computing device 104. In one example, a user may pick up the second computing device 104 to initiate a breathing session, which would be detected by base computing device 102 because the two devices would no longer be in contact with one another. In another example, second computing device 104 may detect a pulse or an interbeat interval and transmit the detected pulse or interbeat interval to base computing device 102.

As shown in FIG. 1B, base computing device 102 may include one or more displays 106. The one or more displays 106 may include a first display 106a that includes one or more lights (e.g., 14 lights 128a-128n as illustrated in FIG. 1F) that are vertically stacked as well as a second display 106b positioned near the top of base computing device 102 and configured to display an instantaneous heart rate from a user and/or other information, such as heart rate variability, time, and/or a session score. In other embodiments, the first and second displays 106a, 106b may be a single display such as an organic light emitting display (OLED) display, micro light emitting diode display, liquid crystal display (LCD), or similar display. Additionally, any number of displays or lights can be used in any configurations or arrangements, including horizontally stacked lights, for example.

Base computing device 102 in some examples may include a power cord 110 which may connect at one end to a power port 112 (see FIGS. 1D and 1C) as well as a power outlet (not shown). Although not shown, base computing device 102 may include a separate lower base that includes a power port, a power cord, and induction charging coils near or surrounding a cradle. The base computing device 102 in these examples may include an upper base, similar to the shown base computing device 102, with corresponding induction coils near the bottom of the upper base as well as one or more batteries. When the induction coils of the upper base are placed near the induction coils of the lower base (e.g., when upper base is place within the lower base's cradle), the one or more batteries of the upper base may be charged. By having this configuration, the upper base may be removed from the lower base and placed in a quiet room where a user could conduct breathing exercises by the biofeedback system 701.

As shown in FIGS. 1C and 1D, base computing device 102 may include one or more audio output devices or speakers 118 positioned at or near lower portion 102b. Base computing device 102 may also include one or more user input buttons 114a, 114b. These user input buttons 114a, 114b can trigger any number of functions including turning on/off the base computing device 102, resetting the base computing device 102, and/or initiating audio, lighted, and/or haptic breathing guide(s). In addition, second computing device 104 may also include one or more user input buttons (e.g., center button 142 illustrated in FIG. 1G). The one or more user input buttons on the second computing device 104 may trigger similar or different functions and/or may trigger different functions depending on how many times or how long one or more of the user input buttons is activated or pressed.

Referring to FIG. 1F, base computing device 102 may include the first display 106a that includes a plurality of lights 128a-128n. Each light 128a-128n may rest on floor 123 or one or more light shelfs 122a-122m. Alternatively, the light shelfs 122a-122m may be one or more light filters configured to separate into a plurality of sections 128a-128n so that they distinguish between different levels of light. The plurality of lights 128a-128n may be attached to the central column 132.

Figures 1G, 1H:
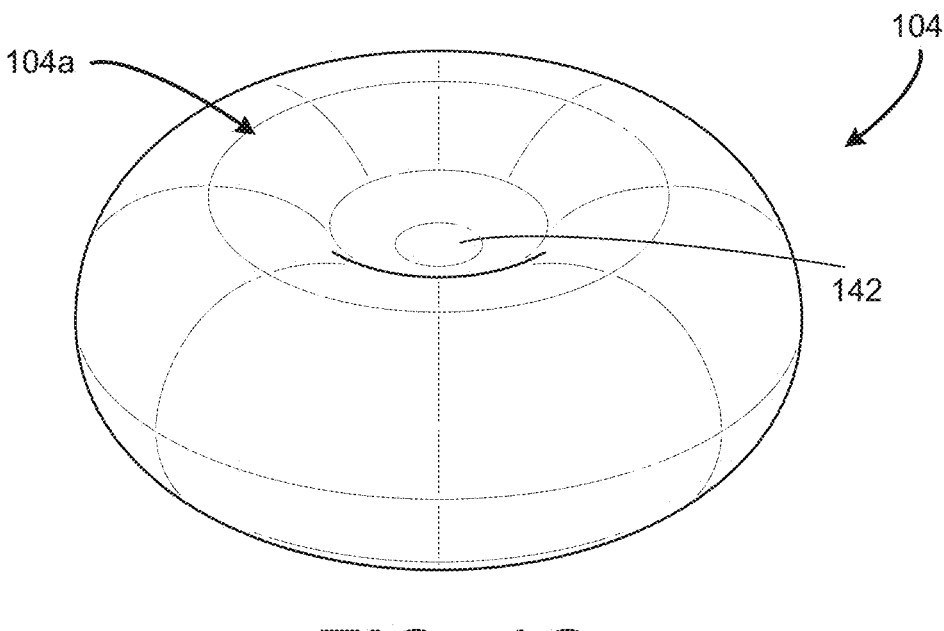
FIG. 1G is a perspective top view of first computing device, in accordance with certain embodiments of the disclosed technology.
FIG. 1H is a bottom view of first computing device, in accordance with certain embodiments of the disclosed technology.

Referring to FIGS. 1G and 1H, second computing device 104 may include center button 142 on its top 104a. In some instances, center button 142 may only be toggled when second computing device 104 is not charging on base computing device 102. The second computing device 104 may include a photoplethysmography (PPG) sensor 146 configured to detect interbeat intervals associated with a user and a strain gauge 144 configured to measure a user's blood pressure when a user applies a first grip 170a (e.g., tight grip) (see FIG. 1I) to the second computing device 104 and gradually loosens a grip or applies a second grip 170b (e.g., loose grip) (see FIG. 1J). First computing device 145 may also include a skin conductivity sensor 145 (e.g., galvanic skin response (GSR) sensor or electrodermal activity (EDA) sensor) configured to measure sweat gland activity in a user's palm, a skin temperature sensor 149 (e.g., a thermometer or thermistor) configured to measure a temperature of a user's palm, and an accelerometer 147 configured to measure motion associated second computing device 104 to generate motion data to help filter data from other sensors. PPG sensor 146, strain gauge 144, skin conductivity sensor 145, skin temperature sensor 149, and accelerometer 147 may be located on or near the bottom 104b of the second computing device 104, although one or more of PPG sensor 146, strain gauge 144, skin conductivity sensor 145, skin temperature sensor 149, and/or accelerometer 147 can also be disposed in other locations.

In some embodiments, second computing device 104 and base computing device 102 may be shaped so that the PPG sensor 146 of second computing device 104 does not contact base computing device 102. Put another way, base computing device 102 may cradle second computing device 104 so that the PPG sensor 146 of second computing device 104 does not contact base computing device 102 while the cradle 102c is in contact with edges of second computing device 104.

As will be described later, a user may initiate one or more breathing sessions using biofeedback system 801. Biofeedback system 801 will provide the user with a default pacer or a default breathing pattern via audio, haptic, and/or visual feedback to guide the user to a resonance state between the baroreceptor reflex and the respiratory sinus arrhythmia. As the biofeedback system 801 collects physiological data (e.g., interbeat interval data), it will change the default breathing pattern to a dynamic breathing pattern and output audio, haptic, and/or visual feedback in accordance with the collected data. In some embodiments, biofeedback system 801 may collect a user's blood pressure prior in order to select an appropriate default breathing pattern for the user or to further adjust a dynamic breathing pattern after user has begun their session.

When sensor data is provided to base computing device 102, base computing device 102 may identify what breathing state the user is in either-parasympathetic or sympathetic based on the data from one or more sensors. For example, data gathered from PPG sensor 146 may quickly (e.g., within seconds or minutes) indicate a parasympathetic state based on a high heart rate variability and a steady or decreasing heart rate or a sympathetic state based on a low heart rate variability and rapid or increasing heart rate. As another example, data gathered from skin conductivity sensor 145 may immediately (e.g., in real-time) indicate a parasympathetic state based on stable or decreasing conductivity (e.g., low sweat gland activity) and a sympathetic state based on increased conductivity (e.g., high sweat gland activity). As another example, data gathered from skin temperature sensor 149 may indicate within over a medium to long term (e.g., minutes to hours) a parasympathetic state based on a gradual rise in temperature (e.g., vasolidation) and a sympathetic state based on a gradual drop in temperature (e.g., vasoconstriction). Base computing device 102 may determine a user's custom/dynamic or default breathing patterns based on any or all of these indications.

Figure 2A:
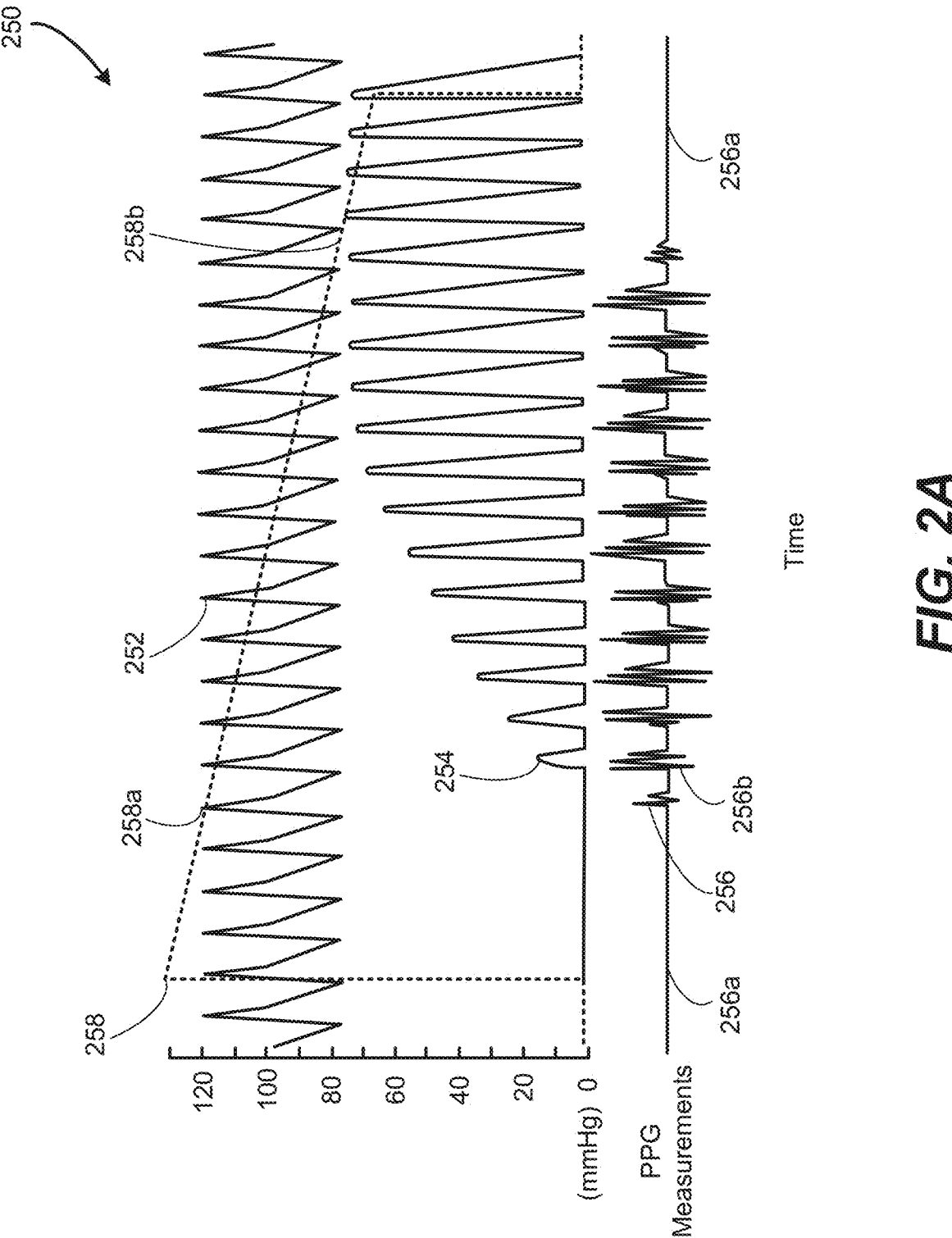
FIG. 2A is a chart showing the effect of grip pressure on blood pressure and PPG measurements, in accordance with certain embodiments of the disclosed technology
Figure 2B:
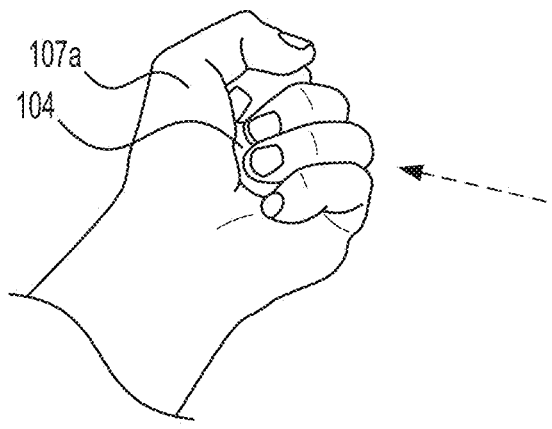
FIG. 2B is a perspective view of first computing device placed in a user's hand with a first grip, in accordance with certain embodiments of the disclosed technology.
Figure 2C:
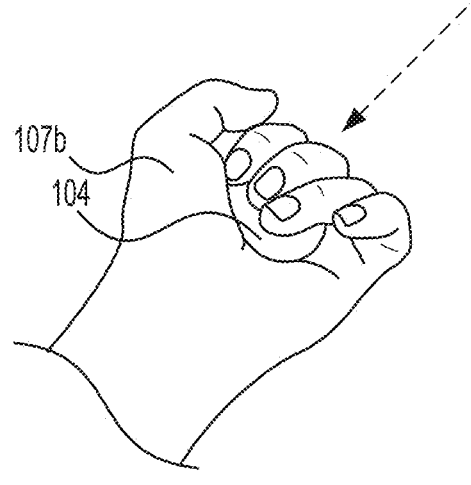
FIG. 2C is a perspective view of first computing device placed in a user's hand with a second grip, in accordance with certain embodiments of the disclosed technology.

FIG. 2A-2C illustrate how biofeedback system 801 may be used to determine a user's blood pressure in order customize a user's breathing pattern. FIG. 2A is a chart 250 showing grip pressure 258 of second computing device 104, arterial pressure 252, arterial flow 254, and PPG measurements 256. When a first grip 270a (e.g., tight grip) (see FIG. 2B) is applied to second computing device 104 by a user, the grip pressure 258 may exceed a maximum of the arterial pressure 252 (or systolic pressure). As the user loosens the first grip 270a (e.g., tight grip) to a second grip 270b (e.g., loose grip) (see FIG. 2C), the grip pressure reduces to a grip pressure point 258a about, or corresponding to just below, a maximum of the arterial pressure 252 or systolic pressure (e.g., approximately 120 mmHg). At this grip pressure point 258a, the PPG sensor 146 may detect unique PPG measurements 256b (e.g., large fluctuations) as opposed to normal or typical interbeat interval measurements 256a. PPG sensor 146 may continue to detect the unique PPG measurements 256b as the grip pressure 258 reduces and until the grip pressure 258 reaches grip pressure point 258b. At grip pressure point 258b, grip pressure 258 is about, or corresponds to just below, a minimum of the arterial pressure 252 or diastolic pressure and the unique PPG measurements 256b subside and more typical PPG measurements 256a resume.

Second computing device 104 can measure grip pressure 258 via strain gauge 144 and PPG measurements 256 via PPG sensor 146. In order to measure a user's blood pressure, a user would tightly grip second computing device 104 until second computing device 104 vibrates and/or base computing device 102 displays a pressure that exceeds approximately 120 mmHg or any other predefined threshold. A user then slowly loosens their grip from the first grip 270a as the strain gauge 144 continues to measure pressure and the PPG sensor 146 monitors for unique PPG measurements 256b. When the first unique PPG measurement(s) 256b are detected, second computing device 104 records, stores, and/or transmits to base computing device 102, strain gauge 144 pressure measurement corresponding to grip pressure point 258a and associating the measurement with initiating unique PPG measurement(s) 256b. Base computing device 102 or second computing device 104 determines a systolic pressure or the highest pressure in the user's arteries when the user's heart beats and pumps blood As the user continues to loosen their relatively first grip 270a (e.g., a tight grip) to be closer to the second grip 270b (e.g., loose grip), the unique PPG measurement(s) 256b disappear, which triggers second computing device 104 to record, and/or transmit to base computing device 102, strain gauge 144 pressure measurement corresponding to grip pressure point 258b and associating the measurement with elimination of unique PPG measurement(s) 256b. Base computing device 102 or second computing device 104 determines diastolic pressure or the minimum pressure in a user's arteries when the user's heart is filling with blood.

Base computing device 102 also can update a user's default breathing or custom (second) breathing pattern based on the user's measured blood pressure. For example, if the user's blood pressure is higher than normal, base computing device 102 may select an initial default breathing pattern with longer exhale and inhale time periods than it would for a user without blood pressure measurements or for a user with low blood pressure measurements.

As previously stated, biofeedback system 801, guide a user to a resonance state between the baroreceptor reflex and the respiratory sinus arrhythmia. Biofeedback system 801 identifies this state my recognizing that a user's instantaneous heart rate corresponds to a smooth, sinusoidal pattern of changes over time. Put another way, biofeedback system 801 detects that a user has entered a resonance state by identifying (i) the presence and predominance of low frequency power as a ratio to all power including low frequency, high frequency, and very low frequency and (ii) exaggerated peak to trough amplitudes. In some instances, biofeedback system 801 may determine that a user has entered resonance state when a person's peak-trough amplitude is consistently 2-4 times a typical peak-trough amplitude.

In some embodiments, second computing device 104 may take one or more standalone measurements of a user's blood pressure. These standalone measurements may not be used to customize a user's breathing pattern or select a default breathing pattern and may be stored and presented to the user in a graphical user interface on a mobile device or other computing device for tracking purposes.

Figure 3:
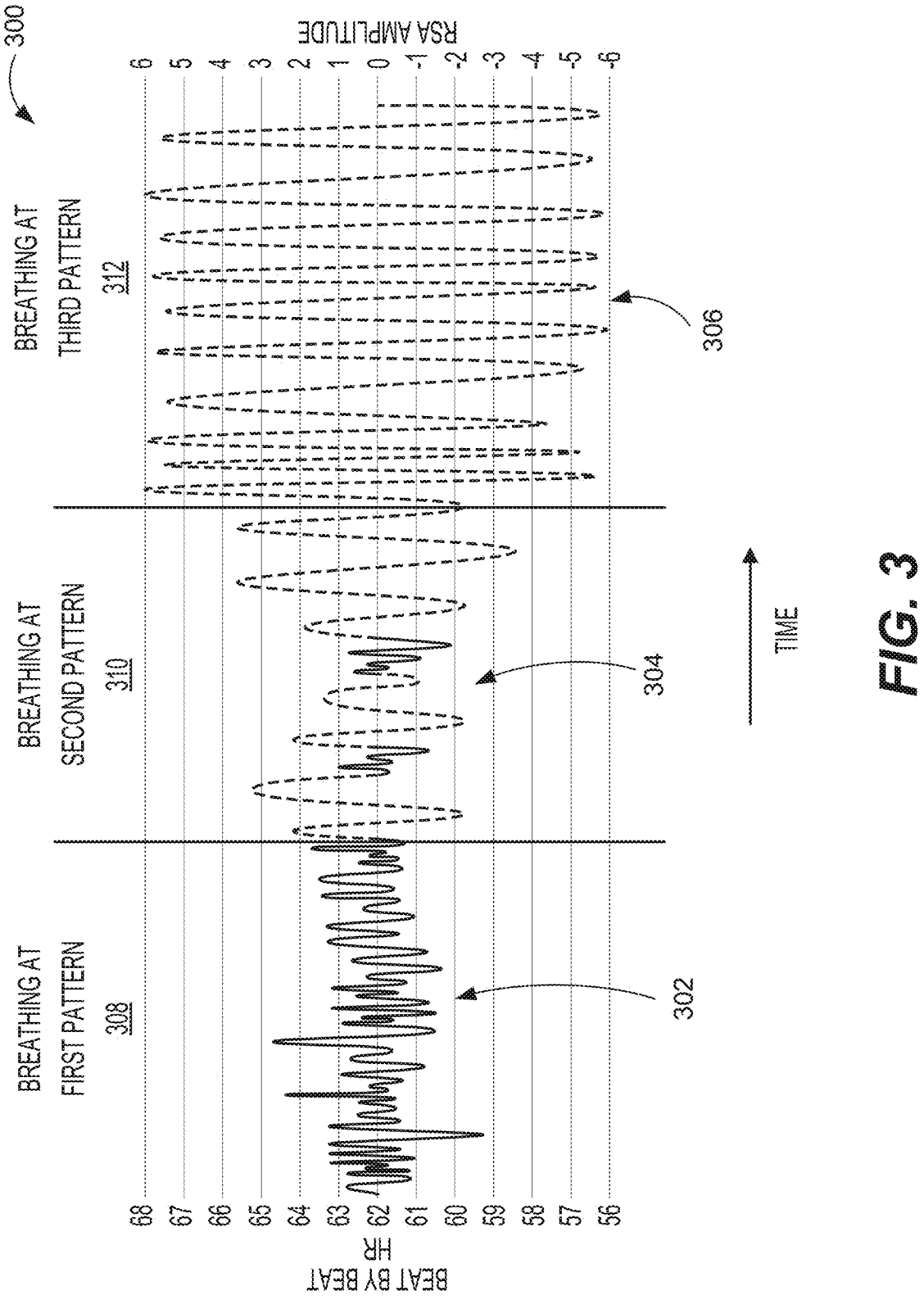
FIG. 3 is a chart showing a user's beat by beat heart rate versus time when using different breathing patterns, in accordance with certain embodiments of the disclosed technology.

FIG. 3 illustrates a chart 300 of a user's instantaneous heart rate (or beat by beat hear rate) measured by biofeedback system 801 against time as well as illustrating respiratory sinus arrhythmia (RSA) amplitudes associated with the measured instantaneous heart rate. Initially biofeedback device 801 may, via second computing device 104, measure a user's resting heart rate 302 associated with a first breathing pattern 308 (a typical or breathing pattern at rest). Biofeedback system 801 may begin instructing a user to breath according to a second pattern 310 or pacer as which time biofeedback device 801 may begin to measure a transition heart rate 304 with some higher RSA amplitudes as well as some RSA amplitude similar to the resting heart rate 302. As biofeedback system 801 gather more physiological data (e.g., instantaneous heart rate changes), biofeedback system 801 may instruct the user to change breathing to a third, which the biofeedback system 801 can dynamically change as it collects and analyzed pattern 312 additional physiological data about the user. Eventually, may reach resonance state and biofeedback system 801 and may measure an associated resonance state heart rate 306 with consistently high RSA amplitudes. FIGS. 4A-4D illustrate various methods for achieving similar measurements shown in FIG. 3 for a user.

Figure 4A:
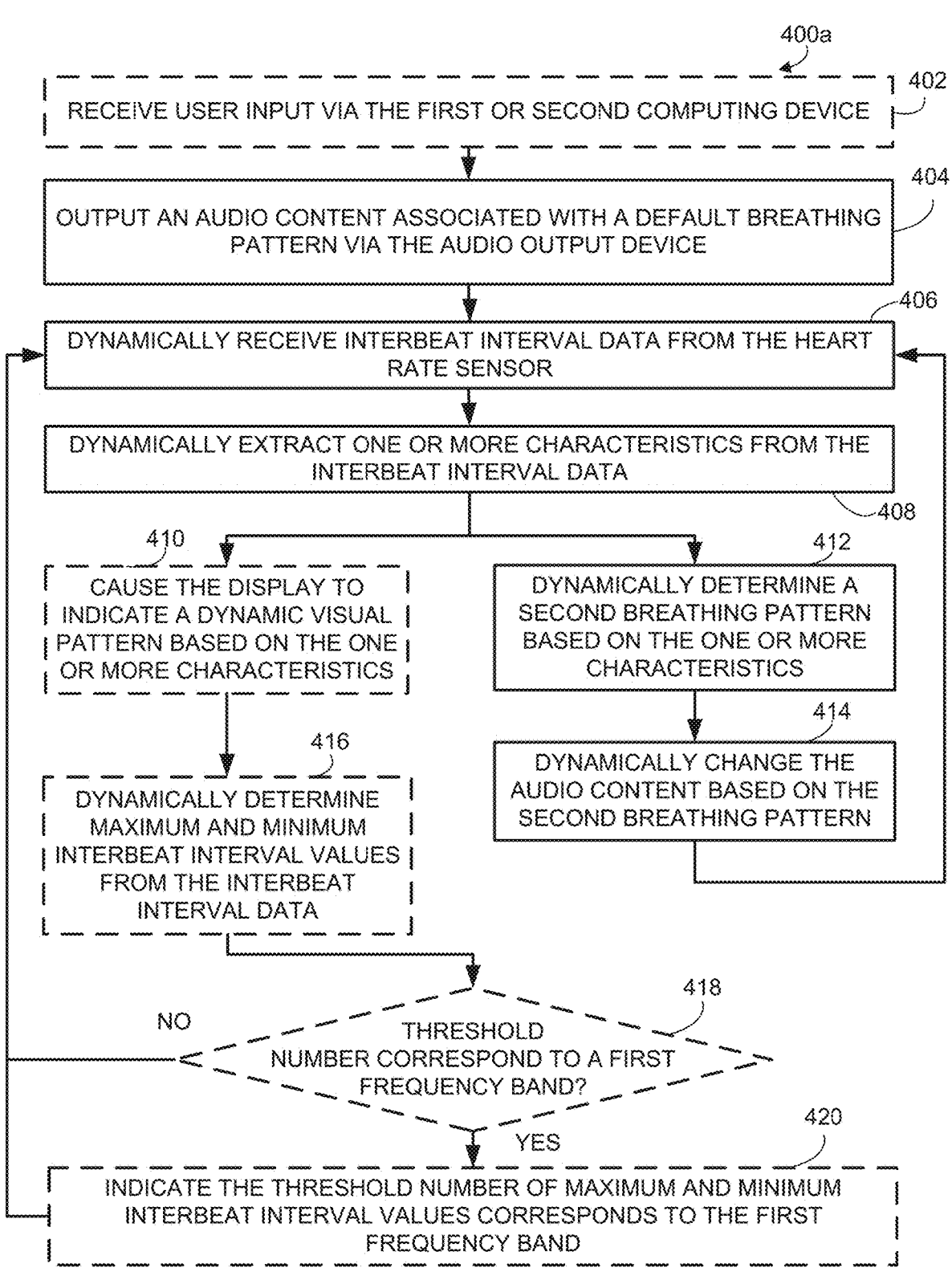
FIG. 4A is a flow diagram illustrating an exemplary method for guiding resonance breathing via audio feedback, in accordance with certain embodiments of the disclosed technology.

FIG. 4A is a flow diagram illustrating an exemplary method 400a for guiding resonance breathing via audio feedback, in accordance with certain embodiments of the disclosed technology. While the steps of method 400a are described as being performed by base (first) computing device 102 for simplicity and brevity, one or more steps may be performed by one or more components of the system 800 (e.g., base (first) computing device 102, second computing device 104, one or more user devices 802, or one or more servers 810), as described in more detail with respect to FIGS. 1A-1H, 4B-4D, 6-8. For example, second computing device 104 may cause components on base computing device 102 to activate such as audio content or display content but perform all other described step. While certain blocks may be identified as being optional, certain embodiments may omit blocks even if they are not necessarily identified as being optional. In addition, blocks (and associated descriptions) may be modified or combined with blocks (and associated descriptions) from other methods in this application and any number of blocks can be executed in a different order than illustrated by way of the examples herein.

In optional block 402, base computing device 102 may receive user input from second computing device 104 or directly from base computing device 102. For example, base computing device 102 may sense that a user removed second computing device 104 away from induction charging coils 105. In another example, a user may press one or more user input buttons 114a, 114b or one or more buttons located on second computing device 104 or may move remote computing device 104, which its movement is detected by an accelerometer.

In an embodiment, second computing device 104 may detect one or more interbeat intervals (or RR intervals) of a user holding or gripping second computing device 104 and send those detected interbeat intervals to base computing device 102. Upon receipt, base computing device 102 may determine whether one or more interbeat intervals equals a threshold number or a threshold amount of time has passed prior to proceeding to block 404.

In block 404, base computing device 102 may output an audio content associated with a default breathing pattern via the audio output device (e.g., integrated speaker 118, headphones, wireless or wired speaker). The audio content may include a series of ascending and descending tones and/or volume, a first set of tones corresponding to breathing in and a second set of tones corresponding to breathing out that is distinct (e.g., different pitch or note) from the first set of tones, melodies or music at desired pace for inhaling and exhaling, voice instructions, or sound corresponding to a person breathing in and out at specific rates. The ascending tones correspond to breathing in and descending tone corresponds to breathing out. In a default breathing pattern, base computing device 102 may output the ascending tones at a first rate and the descending tones at a second rate.

As will be described below, base computing device 102 may change or dynamically change the default breathing pattern to a second breathing pattern such that the first rate changes and/or the second rate changes. In some embodiments, the series of ascending and descending tones may be separated by a series of neural tones at a third rate. The neutral tones may correspond to a user holding their breath. Using the second or dynamic breathing pattern, base computing device 102 may output music or other audio that changes dynamically in pace or pace, pitch, key, texture, structure, dynamics, duration, and/or timbre in response as the second breathing pattern changes.

Figure 5A:
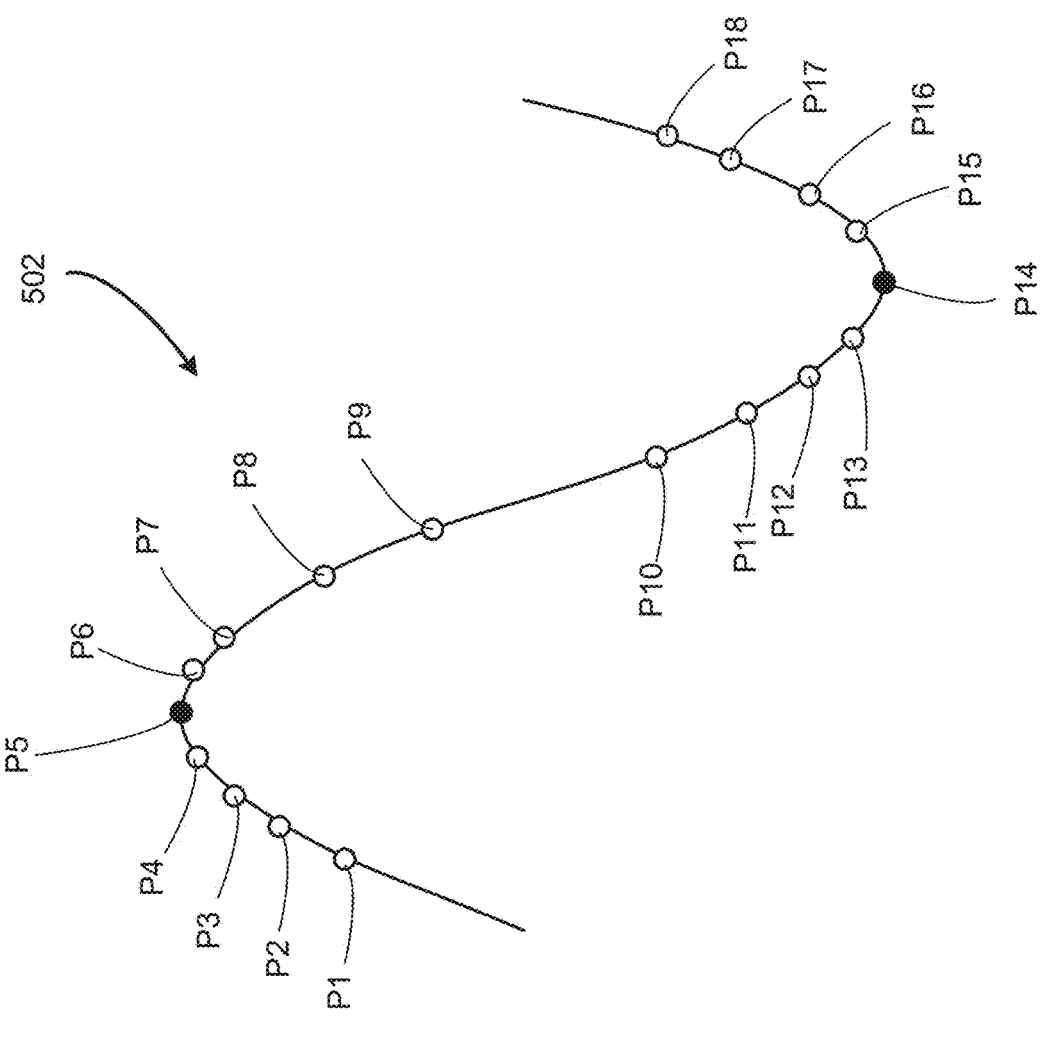
FIG. 5A is a diagram showing how systems and methods identify heartrate peaks and trough, in accordance with certain embodiments of the disclosed technology.
Figure 5B:
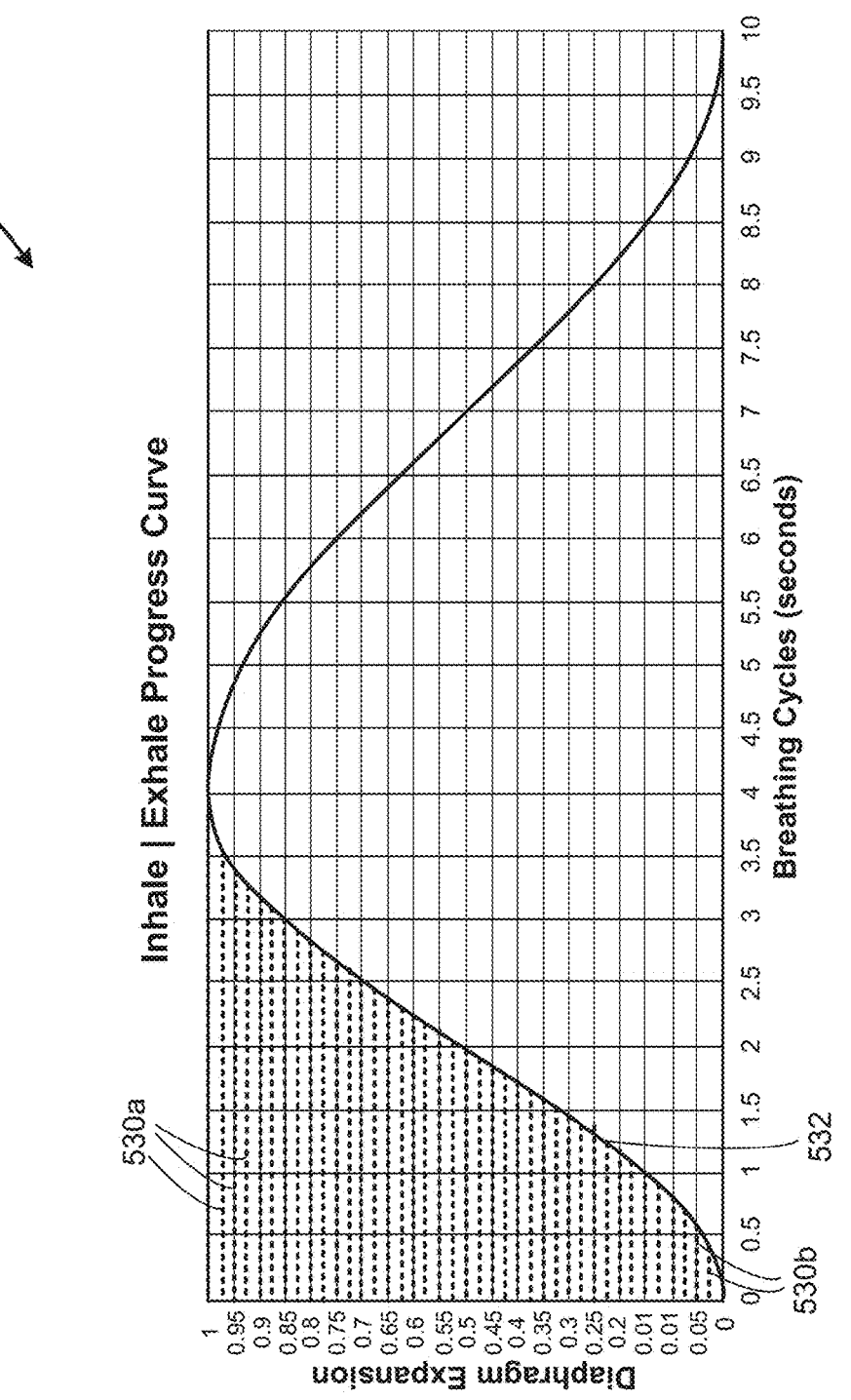
FIG. 5B is a diagram showing an inhale-exhale progress curve plotted over time with exemplary thresholds for changings in audio output volume and/or haptic feedback intensity, in accordance with certain embodiments of the disclosed technology.

FIG. 5B illustrates a chart 525a of a curve 532 if a default breathing pattern or a second breathing pattern where a user's approximate diaphragm expansion (from 0 to 1) is plotted against time in seconds. Chart 525a illustrates exemplary thresholds 530 corresponding to changes in volume (in decibels) of the audio breathing patterns whether it be the default breathing pattern or the second breathing pattern. Each threshold may correspond to a change in diaphragm expansion by 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.20. For a given default breathing pattern or second breathing pattern, base computing device 102 may change the volume of the audio output in accordance with a corresponding inhale-exhale breathing curve. For example, according to exemplary chart 525a, base computing device would increase the volume of the audio output twice based on first thresholds 530b over a 0.5 second period at the beginning of the inhale-exhale breathing curve and would increase the volume of the audio output three times over a 0.5 second period near the peak of the inhale-exhale breathing curve. Although changes in volume are described, base computing device 102 may instruct second computing device 104 to change intensity with respect to haptic feedback based on thresholds 530a, 530b alternatively or in additionally.

Figure 5C:
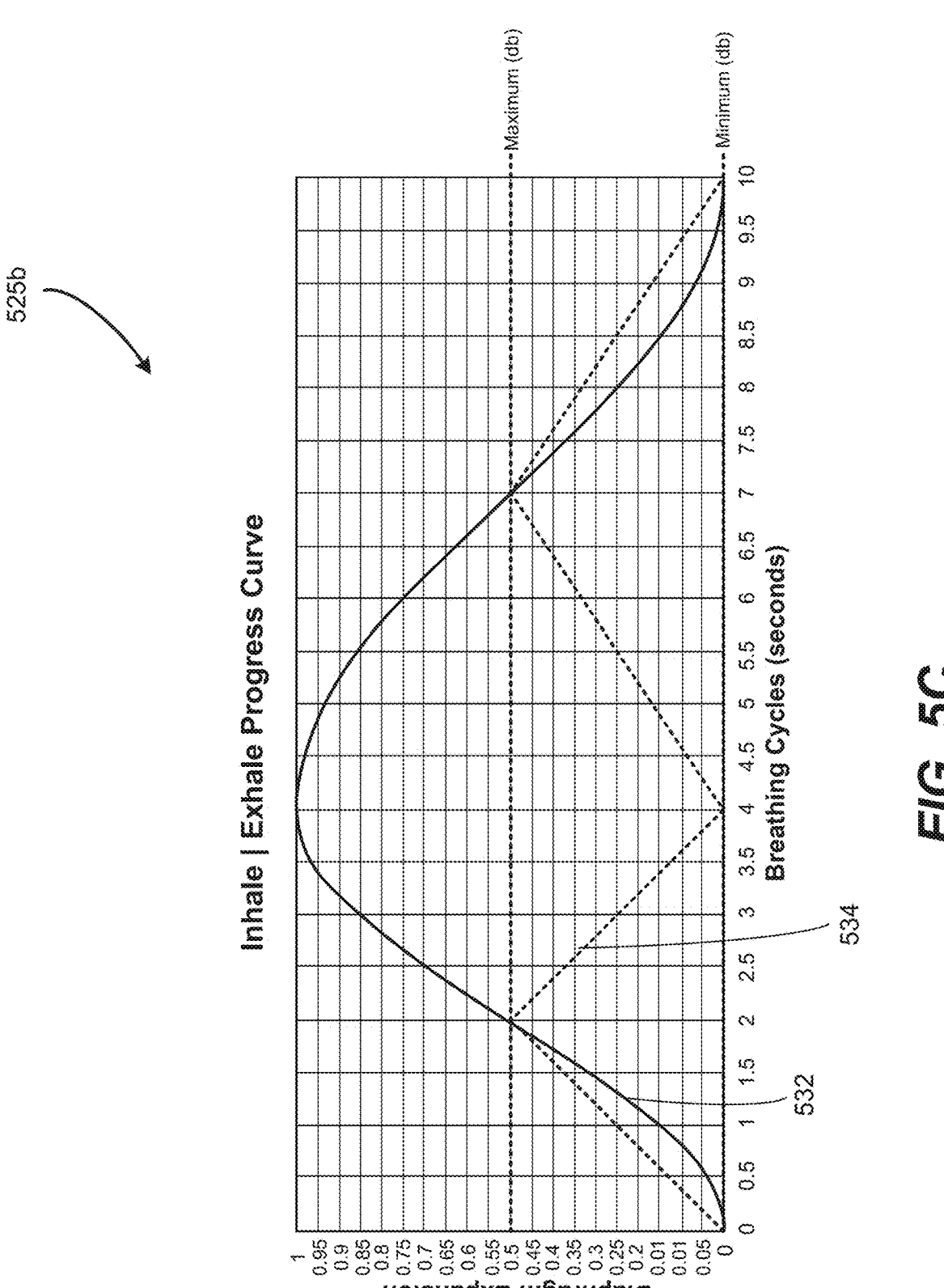
FIG. 5C is a diagram showing an inhale-exhale progress curve plotted and changings in audio output volume over time, in accordance with certain embodiments of the disclosed technology.

FIG. 5C is a chart 525b showing curve 532, but with maximum volume of the audio output corresponding to a halfway point (0.5) in the inhale diaphragm expansion and a second halfway point (0.5) in the exhale diaphragm expansion. Similarly, chart 525b shows a curve 532 with a minimum volume at the minimum (0) and highest diaphragm (1) expansion positions. Base computing device 102 may guide a user during inhale to increase the volume of the audio content associated with a default breathing pattern or second breathing pattern until a halfway point (0.5) in the diaphragm expansion and then start decreasing the volume of the audio content until peak in diaphragm expansion (1). Then, base computing device 102 may guide a user during exhale to increase the volume of the audio content associated with a default breathing pattern or second breathing pattern until a halfway point (0.5) in the diaphragm expansion and then start decreasing the volume of the audio content until minimum or through in diaphragm expansion (0).

Put another way, base computing device 102 may trigger a change in volume of the audio output associated with the default breathing pattern or second breathing pattern in response to determining that the diaphragm expansion percentage changed by a threshold diaphragm expansion percentage. The change in volume of the audio output during an inhale portion of the default breathing pattern or the second breathing pattern correspond with increases in volume until the diaphragm expansion percentage reaches a first threshold (e.g., approximately 50% of diaphragm expansion) and then corresponds with decreases in volume until the diaphragm expansion percentage reaches a second threshold (e.g., approximately 100% of diaphragm expansion). The volume change during an exhale portion of the default breathing pattern or second breathing pattern correspond with increases in volume until the diaphragm expansion percentage reaches a third threshold (e.g., approximately 50% of diaphragm expansion) and then corresponds with decreases in volume until the diaphragm expansion percentage reaches a third threshold (approximately 0% of diaphragm expansion). Although changes in volume are described, base computing device 102 may instruct second computing device 104 to change intensity with respect to haptic volume pattern shown.

The voice instructions may include instructions to prepare for breathing (e.g., "We are going to breathe in for a count of four, hold for a count of three, and breathe out for a count of four. Let's begin."), breathe in for an amount of time (e.g., "breathe in, one, two, three, four"), hold for an amount of time (e.g., "hold, one, two, three, four"), or breathe out for an amount of time (e.g., breathe out, one, two, three, four"). Much like the ascending, neutral, and descending tones described above, base computing device 102 may, following a breath in, a breath out, and/or a hold voice guidance, output voice count tone(s) at the first rate, the second rate, and/or the third rate in a default breathing pattern. In some embodiments, voice instructions may include a pre-recorded instructor, computer generated voice instructions, or artificial intelligence (AI) generated voice instructions.

In some embodiments, the audio content may begin with voice instructions to prepare for breathing and proceed to using a series of tones that include a combination of ascending, neutral, and/or descending tones. In other embodiments, the audio content may switch between voice instructions and a series of tones after one or more cycles (breathe in, hold, breathe out). The audio content may include spoken feedback about current interbeat interval data (e.g., "you're doing well," "you're moving into a parasympathetic state," and/or "you've reached resonance breathing").

In block 406, base computing device 102 may dynamically receive interbeat interval data from first physiological sensor 712 such as a heart rate sensor (e.g., PPG sensor 146). Second computing device 104 may dynamically detect interbeat intervals and dynamically generate interbeat interval data and/or an instantaneous heart rate using first physiological sensor 712 when a user holds or grips the second computing device 104. In other embodiments, a user may place second computing device 104 on a finger or around a wrist (e.g., a wrist band or watch) to obtain a consistent reading. Second computing device 104 may dynamically and continuously transmit (wirelessly or via a wire) the interbeat interval data to base computing device 102, which dynamically receives it.

In block 408, base computing device 102 may dynamically extract or determine one or more characteristics from the interbeat interval data. For example, base computing device 102 may extract or determine elapsed time, a heart rate, a change in heart rate, a peak amplitude, a trough amplitude, and/or a frequency between adjacent peaks and adjacent troughs. Base computing device 102 may also filter out noise such as ectopic beats or beats caused by electronic devices or communicating wireless devices. The peak amplitude corresponds to the maximum heart rate over a given time period (e.g., about 1-12 seconds) whereas the trough amplitude corresponds to the minimum heart rate over a given time period.

In some embodiments, base computing device 102 may determine one or more characteristics from the interbeat interval data such as peak amplitudes (also referred to as peaks) or trough amplitudes (also referred to as troughs or valleys) by comparting each heartbeat to nearby or adjacent heartbeats. Referring to FIG. 5A, base computing device 102 identifies heartbeats on an interbeat interval wave 502. Base computing device 102 identifies a heartbeat as a peak or trough by comparing a heartbeat's heart rate value relative to four neighboring heartbeat heart rate values and the next in time heartbeat position. Base computing device 102 determines that a first heartbeat P5 is at a peak heart rate position when it is the maximum heart rate compared to two heartbeats (P4, P3) immediately before and two heart beats (P6, P7) immediately after the first heartbeat P5 and the heart rate of the first heartbeat P5 is not equal to the heart rate of heartbeat immediately after the first heartbeat P6. Similarly, base computing device 102 determines that a second heartbeat P14 is at a trough position when it is the minimum heart rate compared to two heartbeats (P13, P12) immediately before and two heartbeats (P15, P16) immediately after the second heartbeat P14 and the heart rate of the second heartbeat P14 is not equal to the heart rate value of the heartbeat immediately after the second heartbeat P14. However, base computing device 102 determines that a third heartbeat P6 is not a peak heartbeat when its heart rate value is not greater than at least one of its four immediately-neighboring heartbeats (P4, P5, P7, P8). In other words, base computing device 102 determines that the heart rate value of heartbeat P6 is not greater than the heart rate value of heartbeat P5. Other methods for identifying a heartbeat as a peak or trough can also be used in other examples, including other numbers of adjacent heart rate values.

Referring back to FIG. 4A, in optional block 410, base computing device 102 may cause display 106 to indicate a dynamic visual pattern based on the one or more characteristics. For example, base computing device 102 may illuminate one or more of the plurality of lights 128a-128n in accordance with the dynamic visual pattern starting from the first light 128n to the last light 128a. Base computing device 102 may determine the dynamic visual pattern by determining a display position (e.g., how many of the lights 128a-128n are turned on starting from the bottom) and a display rate (e.g., time for a display position to change) from the one or more characteristics.

The dynamic visual pattern may be determined based on the one or more changes in heart rate such as identifying a change from increasing to decreasing heart rate (e.g., a peak interbeat interval) or from a decreasing to increasing heart rate (e.g., a trough interbeat interval) For example, base computing device 102 may identify a peak interbeat interval at 60 beats per minimum (bpm) and an adjacent or next minimum of 52 bpm. Computing device 102 may also identify that it took 6 seconds for the heart to go from 60 bpm to 52 bpm. As such, base computing device 102 may illuminate one or more lights 128a-128n over a similar period. For example, over the next six second period, base computing device 102 may illuminate first light 128n after 2 seconds, first and second lights 128n, 128m after 4 seconds, and lights 128n, 128m, and 128l after 6 seconds. Put another way, the light would take 6 seconds to go from position 'X' to position "X-8" (or zero if starting position was 8 or less). In some embodiments, base computing device 102 determines the display position corresponding to the current position of the lights (e.g., lights 128n, 128m, and 128l are illuminated). For example, base computing device 102 may determine a first peak amplitude of 3 and illuminate lights 128n, 128m, and 128l at a first rate about 2 seconds. Base computing device 102 may next determine a first trough amplitude of −3 and turn off or dim lights in order from 128l, 128m, and 128n at a rate of about 2.07 seconds based on a difference in amplitude of heart rate changes. Base computing device 102 may next determine a second peak amplitude of 4 and turn on lights 128n, 128m, 128l, 128k at a first rate about 1.96 seconds. However, if base computing device 102 determines that a trough amplitude causes the display position to be less than zero, base computing device 102 can round the display position to zero while preserving the timing of how quickly the display positions moved to zero.

In block 412, base computing device 102 may dynamically determine a second breathing pattern based on the one or more characteristics. Base computing device 102 may determine the second breathing pattern by determining a weighted average of rates associated with peak interbeat intervals and trough interbeat intervals. The weighting criteria may be based upon the frequency at which the rates occur, the amplitude (e.g., power) associated with each rate, or a combination thereof. Rates may be associated with a partial breathing cycle (e.g., an inhale or an exhale) or a full breathing cycle. Similarly, base computing device 102 may dynamically determine the second breathing pattern by determining a rolling weighted average based on continually received interbeat interval data as described above with reference to block 406. The second breathing pattern may include one frequency (e.g., 6 breaths per minute) or may include a partial frequency (e.g., 4 seconds for breathing in, and 6 seconds for breathing out). The latter would also be associated with 6 breaths per minute (which approximately equates to 10 seconds per breath).

In an embodiment, base computing device 102 removes or ignores peaks and troughs (see FIG. 5) that are outside of (e.g., lower than) a low frequency threshold. Base computing device 102 may then determine a plurality of trough to peak wave segments and associated them as an inhale and with a time segment. Base computing device 102 may also determine a plurality of peak to trough wave segments and associate them as exhales and with a time segment. Base computing device 102 may take the weighted averages of time segments respectively associated with the inhales and exhales to calculate inhale and exhale times for the second breathing pattern. In some examples, base computing device 102 determines the weighted averages dynamically and updated the second breathing pattern dynamically as new data (e.g., new interbeat interval data) is received and processed.

In block 414, base computing device 102 may dynamically change the audio content based on the second breathing pattern. For example, base computing device 102 may change the first, second, and/or third rates. Blocks 406, 408, 412, and/or 414 may run simultaneously with optional blocks 410, 416, 418, and/or 420 and may repeat iteratively until second computing device 104 is placed near base computing device's 102 induction charging coils 105, base computing device 102 receives user input ending a breathing session, base computing device 102 fails to receive interbeat interval data from second computing device 104 over a threshold time period (e.g., second computing device 104 does not receive interbeat interval data for about 30 seconds, about 60 seconds, about 90 second, about 120 seconds, etc.), or any other termination criterion is satisfied.

In optional block 416, base computing device 102 may dynamically determine or a number of maximum (peaks) and minimum interbeat interval values (troughs) from the interbeat interval data. In some embodiments, this step may be simultaneously done with block 408. Block 408 may involve extracting peaks and troughs (or other data physiological data) from the interbeat interval data whereas block 416 involves determining, associating, or categorizing a number or groups of adjacent peaks and troughs for threshold comparison in block 208.

In optional block 418, base computing device 102 may determine whether a threshold number of maximum and minimum interbeat interval values correspond to a first frequency band. For example, base computing device 102 may determine that when about 70% to about 95% (e.g., about 75%, about 80%, about 85%, about 90%, or about 95%) of the last 4-20 (e.g., 4, 5, 6, 7, 8, 9, 10, 11, 12, 13, 14, 15, 16, 17, 18, 19, 20) changes between maximum and minimum interbeat interval values corresponds to frequencies of about 2.4 and about 9.5 (e.g., about 4.5 to about 7.5) cycles or half cycles per minute. If base computing device 102 determines that the threshold number of maximum and minimum interbeat interval values does not correspond to the first frequency band (i.e., optional determination block 418=NO), blocks 206, 208, 210, 216 and 218 may iteratively repeat based on newly received interbeat interval data until base computing device 102 determines that the threshold number of maximum and minimum interbeat interval values corresponds to the first frequency band (i.e., optional determination block 418=YES) or second computing device 104 is placed near base computing device's 102 induction charging coils 105, base computing device 102 receives user input ending a breathing session, base computing device 102 fails to receive interbeat interval data from second computing device 104 over a threshold time period (e.g., second computing device 104 does not receive interbeat interval data for about 30 seconds, about 60 seconds, about 90 second, about 120 seconds, etc.), or another terminal point is reached. If base computing device 102 determines that the threshold number of maximum and minimum interbeat interval values corresponds to the first frequency band (i.e., optional determination block 418=YES), base computing device 102 may proceed to optional block 220.

In optional block 420, base computing device 102 may indicate the threshold number of maximum and minimum interbeat interval values corresponds to the first frequency band (e.g., the user has reached resonance breathing). In some embodiments, base computing device 102 may cause display 126 to display the dynamic visual pattern (e.g., turn on one or more lights 128a-128n as a first color such as blue or red), but may indicate the threshold number of maximum and minimum interbeat interval values are in the first frequency band by turning the one or more lights 128a-128n to a second color (e.g., green). In some embodiments, base computing device 102 may display a topmost light (e.g., light 128a-128n) in a different color than the other lights as it moves up the column once the threshold number of maximum and minimum interbeat interval values for the user corresponds to the first frequency band (e.g., the user has reached resonance breathing).

In other embodiments, base computing device 102 may indicate the threshold number of maximum and minimum interbeat interval values are in the first frequency band by making an audio change (e.g., a ding, a voice instruction, or other audio cue), a display change (e.g., changing colors of one or more lights 128a-128n, indicating resonance breathing on display 106b), a haptic feedback change, or a combination thereof. Blocks 406, 408, 410, 416, 418, and 420 may run simultaneously with blocks 412 and 414 and may repeat iteratively until second computing device 104 is placed near base computing device's 102 induction charging coils 105, base computing device 102 receives user input ending a breathing session, base computing device 102 fails to receive interbeat interval data from second computing device 104 over a threshold time period (e.g., second computing device 104 does not receive interbeat interval data for about 30 seconds, about 60 seconds, about 90 second, about 120 seconds, etc.), or another terminal point is reached. In some embodiments, base computing device 102 may display a topmost light (e.g., one of lights 128a-128n) in a different color (e.g., green) than the other lights as they turn on and off up or down the column once the user has reached resonance breathing. In this case, the pacer light may be a different color (blue) from the progress light (e.g., green). The pacer light is associated with a default or dynamic breathing pattern whereas the process light indicates to the a user that they have reaches resonance breathing state or the minimum and maximum interbeat interval values correspond to a first or threshold frequency band.

Figure 4B:
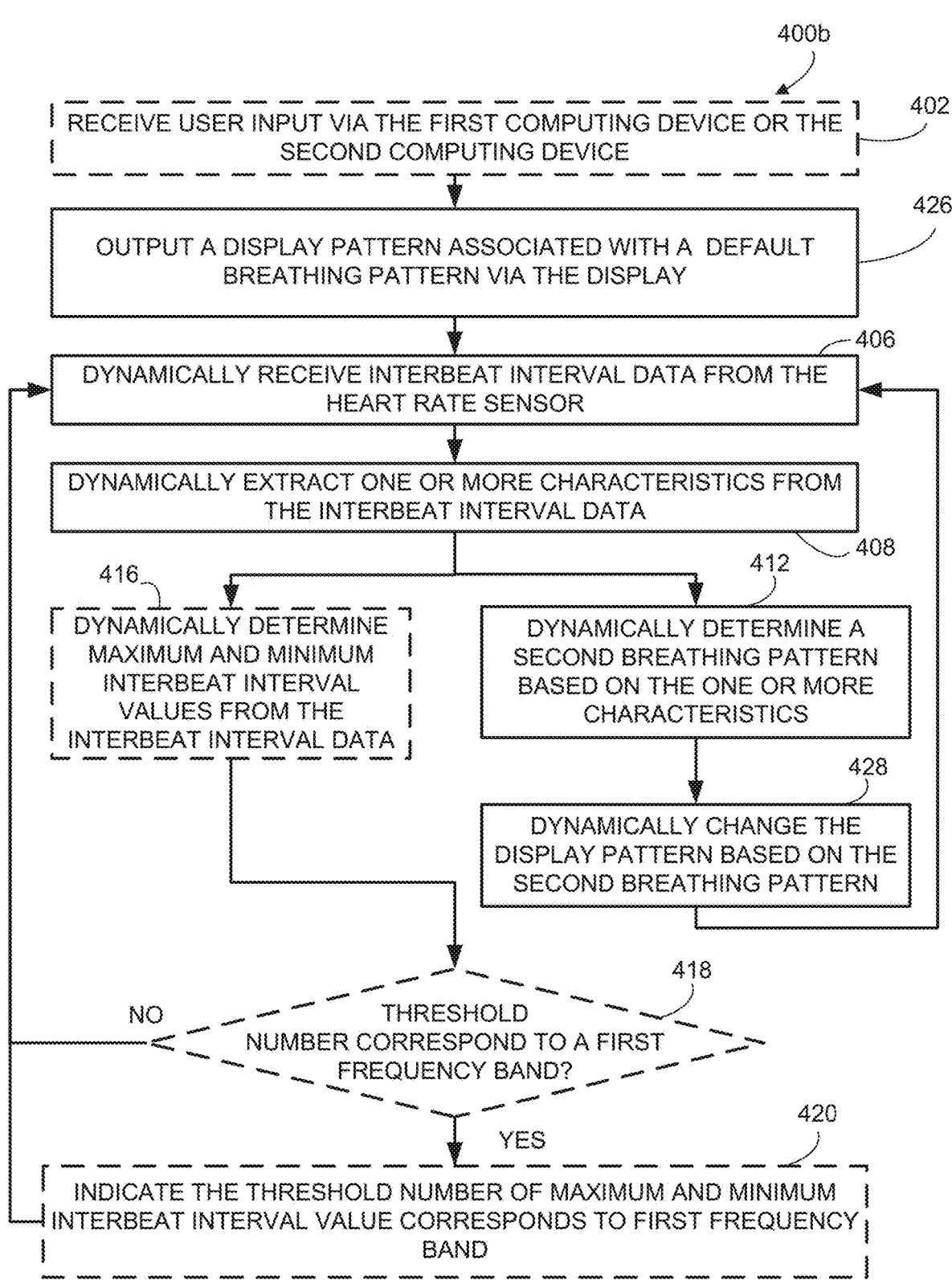
FIG. 4B is a flow diagram illustrating an exemplary method for guiding resonance breathing via visual feedback, in accordance with certain embodiments of the disclosed technology.

FIG. 4B is a flow diagram illustrating an exemplary method 400b for guiding resonance breathing via visual feedback, in accordance with certain embodiments of the disclosed technology. Method 400b overlaps with method 400a in that method 400b also contains blocks 402, 406, 408, 412, 416, 418, and 420. The descriptions of those steps are found above and not repeated herein for brevity. However, method 400b also includes blocks 426 and 428, which are not found in method 400a and are described below.

In block 426, base computing device 102 may output a display pattern associated with a default breathing pattern or default pacer on display 106 (e.g., a plurality of lights 128a-128n). The default breathing pattern may correspond to lights 128a-128n turning on in an ascending order starting from the lowest light 128n of the one or more lights 128a-128n and then turning off in a descending order starting with the highest positioned light of the one or more lights 128a-128n that is turned on. The ascending pattern corresponds to a breathing pattern with the one or more lights 128a-128n. The one or more lights 128a-128n may turn on at a first rate and turn off at a second rate. In some embodiments, the lights may pulse or pause turning off or on to correspond to a user holding their breath.

In some embodiments, base computing device 102 may indicate progress how close a user is to having a threshold number of maximum and minimum interbeat interval values corresponds to the first frequency band (e.g., resonance breathing). In some embodiments, base computing device 102 may display both the default pacer and an indication that the user has reached a resonance breathing state. In this case, base computing device 102 may indicate the user has reached a resonance breathing state by turning the upper most light in the pacer of the one or more lights 128a-128n to a second color (e.g., green) while keeping the other pacer lights (e.g., lights 128a-128n other than upper most) a first color (e.g., blue or red). In some embodiments, the default breathing pattern of the lights turning on or off may be sinusoidal.

In block 428, base computing device 102 may dynamically change the display pattern based on the second breathing pattern or second pacer. For example, base computing device 102 may change the first rate, the second rate, and/or the duration of the pulsing of, and/or pause, the one or more lights 128a-128n. In some embodiments, base computing device 102 may display both the second pacer and an indication that the threshold number of maximum and minimum interbeat interval values are in the first frequency band for a user (e.g., the user has reached a resonance breathing state). In this case, base computing device 102 may turn the upper most light in the second pacer of the one or more lights 128a-128n to a second color (e.g., green) while keeping the other pacer lights (e.g., lights 128a-128n other than upper most) a first color (e.g., blue or red). In some embodiments, the second breathing pattern of the lights turning on or off may be sinusoidal.

Similar to FIG. 4A, blocks 406, 408, 412, 416, 418, 420, and 428 of FIG. 4B may iteratively repeat until second computing device 104 is placed near base computing device's 102 induction charging coils 105, base computing device 102 receives user input ending a breathing session, base computing device 102 fails to receive interbeat interval data from second computing device 104 over a threshold time period (e.g., second computing device 104 does not receive interbeat interval data for about 30 seconds, about 60 seconds, about 90 second, about 120 seconds, etc.), or another terminal point is reached.

Figure 4C:
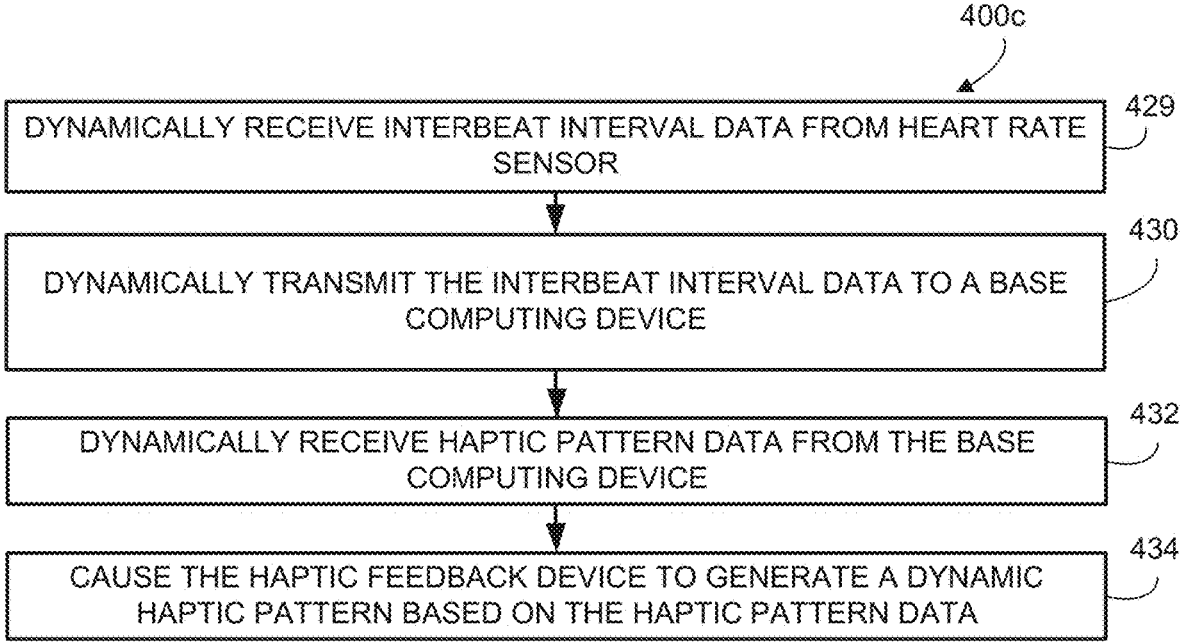
FIG. 4C is a flow diagrams illustrating an exemplary method for guiding resonance breathing via haptic feedback, in accordance with certain embodiments of the disclosed technology.

FIG. 4C is a flow diagrams illustrating an exemplary method 400c for guiding resonance breathing via haptic feedback, in accordance with certain embodiments of the disclosed technology.

In block 429, second computing device 104 may dynamically receive interbeat interval data from first physiological sensor 712 such as a hear rate sensor (e.g., the PPG sensor 146). Second computing device 104 may dynamically detect instantaneous heart rate and dynamically generate interbeat interval data using first physiological sensor 712 when a user maintains contact with first physiological sensor 712 (e.g., the user holds the second computing device 104 in their hand).

In block 430, second computing device 104 may dynamically transmit the interbeat interval data to base computing device 102. Second computing device 104 may transmit the interbeat interval data to base computing device 102 via wireless or wired connection.

In block 432, second computing device 104 may dynamically receive haptic pattern data from base computing device 102 via wireless or wired connection. The haptic feedback pattern data may correspond to the breathing pattern with ascending intensity and/or frequency of vibration output (e.g., instructions to fire more frequently) when a user is instructed to breathe in and decreasing intensity and/or frequency of vibration output (e.g., instructions to fire less frequently) when a user is instructed to breath out or other haptic patterns described throughout this application.

In block 434, second computing device 104 may cause haptic feedback generator 411 to generate a dynamic haptic pattern based on the haptic pattern data.

Figure 4D:
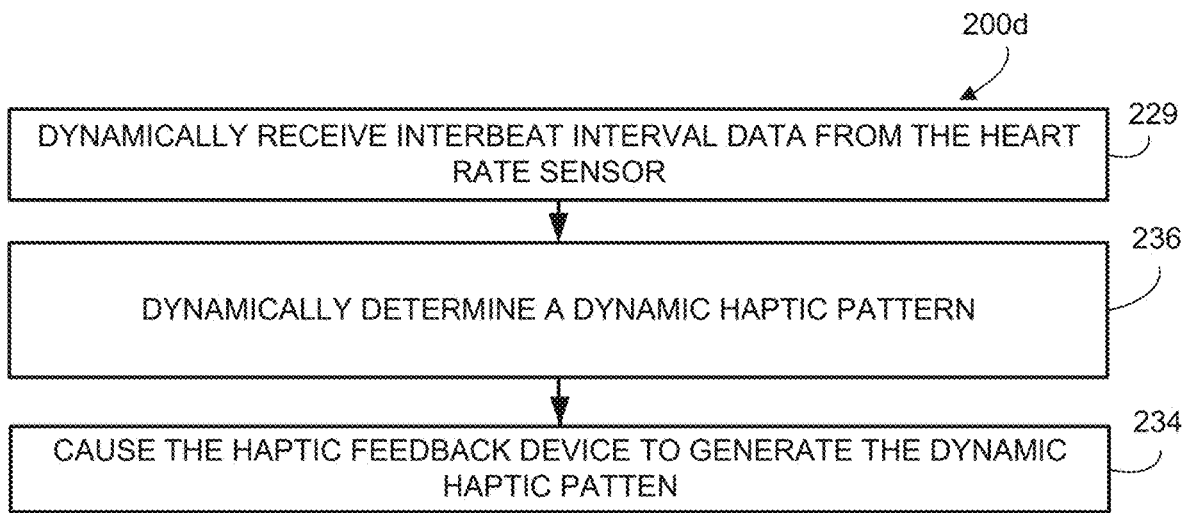
FIG. 4D is a flow diagrams illustrating an exemplary method for guiding resonance breathing via haptic feedback, in accordance with certain embodiments of the disclosed technology.

FIG. 4D is a flow diagrams illustrating an exemplary method for guiding resonance breathing via haptic feedback, in accordance with certain embodiments of the disclosed technology. Method 400d overlaps with method 400c in that method 400d also contains blocks 429 and 434. The descriptions of those steps are found above and not repeated herein for brevity. However, method 400d also includes block 436 which is not found in method 400c and is described below.

In block 436, second computing device 104 may dynamically determine a dynamic haptic pattern. For example, the dynamic haptic pattern may include an ascending pattern and a descending pattern corresponding to a guide for the user's breathing (see e.g., second breathing pattern above).

Second computing device 104 may change a rate and/or intensity (e.g., strength) associated with an ascending haptic pattern and a rate and intensity associated with a descending pattern.

In some embodiments, base computing device 102 or second computing device 104 may monitor physiological data from one or more physiological data sensors (e.g., first and/or second physiological sensor 712, 713) to determine whether any physiological data meets a threshold or threshold range (e.g., increasing, decreasing, or stabilizing). In response to the base computing device 102 or second computing device 104 determining one or more measurements meet a threshold or threshold range, base computing device 102 or second computing device 104 may determine or select a corresponding audio, haptic, and/or visual feedback and output the selected audio, haptic, and/or visual feedback.

In some embodiments, base computing device 102 or second computing device 104 may generate (e.g., using AI) a custom audio, haptic, or visual feedback for output associated with the threshold. The feedback may be incentives (e.g., instructing a user they are making progress), guidance (e.g., instructing a user to take a deep breath), feedback (e.g., displaying a heartrate), or rewards (e.g., instructing the user that have achieved a milestone such as reached a resonance breathing state). Some non-limiting examples of physiological sensors that used may include to generate physiological data used in feedback determinations may include a palm temperature sensor (e.g., via in the form of a metallic ring, such as one made with copper, and similar to strain gauge 144), a skin conductance sensor, a non-invasive blood pressure sensor (e.g., strain gauge 144), a musculoskeletal sensor, an oxygen saturation (SpO2) sensor, a capnometer, a cortisol sensor, a electroencephalogram (EEG) sensor, an electromyogram (EMG) sensor, a photoplethysmography (PPG) sensor (e.g., PPG sensor 146), a pressure sensor, and a breathing rate sensor (e.g., Tidal volume sensor). Some additional sensors may include an accelerometer configured to provide motion data in order to clean interbeat interval data or other data from one or more other sensors (e.g., PPG sensor 146 or heart rate sensor).

Base computing device 102 or second computing device 104 may monitor any of the following physiological data, measurements, or metrics to determine whether thresholds are met (e.g., increasing, decreasing, or stabilizing) and trigger audio, haptic, and/or visual feedback when one or more thresholds are met: (i) resting heart rate measurements, (ii) respiratory sinus arrhythmia (RSA) measurements, (iii) consecutive low frequency oscillation measurements, (iv) amplitudes of RSA, (v) heart rate variability (HRV) metrics (e.g., low power root mean square successive difference (RMSSD) or percentage of successive normal cardiac interbeat intervals greater than 50 milliseconds (pNN50)), (vi) skin conductance measurements, (vii) blood pressure measurements, (viii) skin temperature measurements, (ix) breathing rate (e.g., tidal volume), (x) heart metrics (e.g., interbeat intervals), (xi) EMG measurements, (xii) EEG measurements, (xiii) SpO2 measurements, (xiv) carbon dioxide measurements, (xv) cortisol measurements, and (xvi) capillary refill time. For example, if base computing device 102 determines that a user's respiratory sinus arrhythmia (RSA) measurements stabilizes within a threshold range for a threshold period of time or a user's breathing rate decreases by a threshold amount, then the base computing device 102 may determine a stored audio (e.g., spoken words such as: "You're doing great!" or a sound effect such as a chime) corresponding to the change or trend and output the corresponding audio on a speaker 118 of base computing device 102. As another example, if base computing device 102 determines that a user's instantaneous heart rate increases beyond a threshold level, base computing device 102 may determine that a different stored vocal audio feedback ("Now we are going to take a deep breath") corresponds to the increased heart rate and output the feedback.

Figure 6:
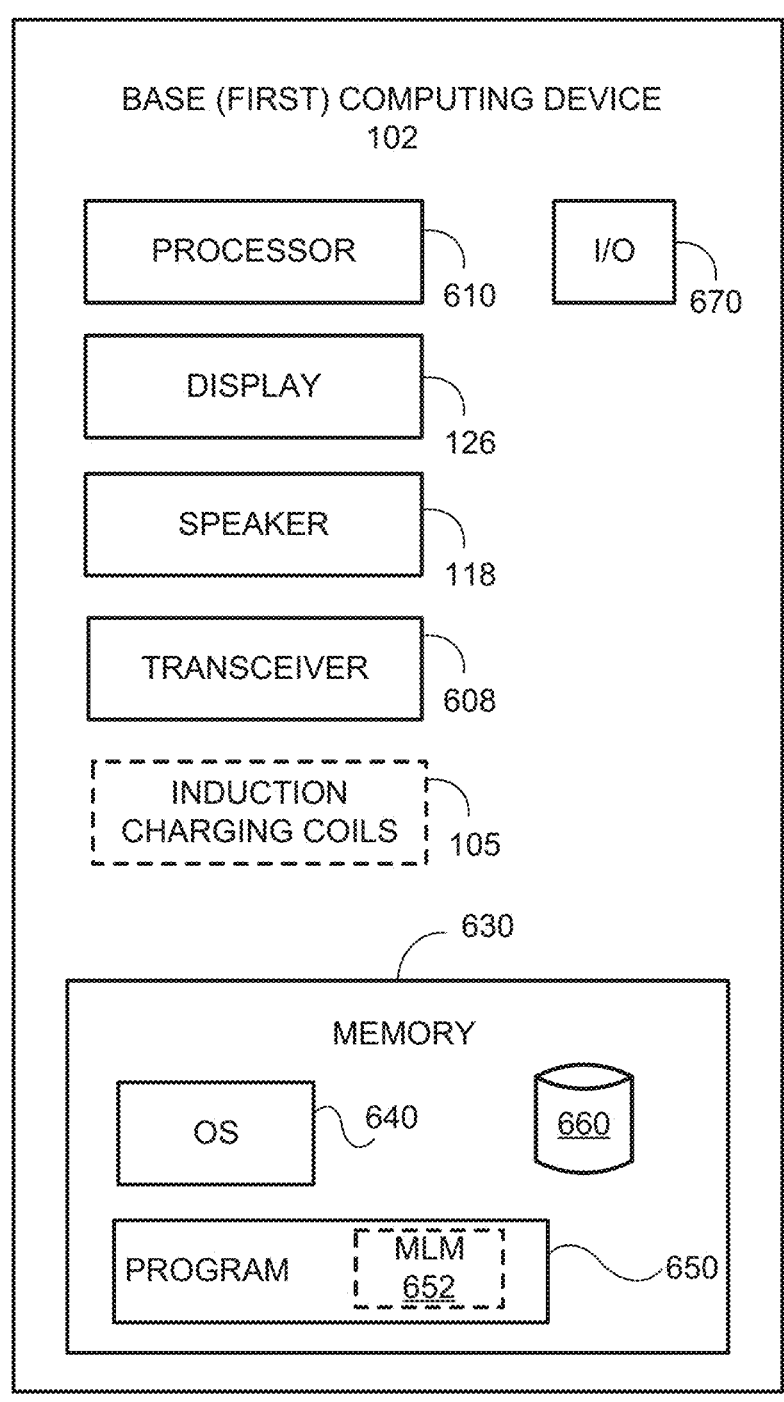
FIG. 6 is a block diagram of an example base computing device, according to an example implementation of the disclosed technology.
Figure 8:
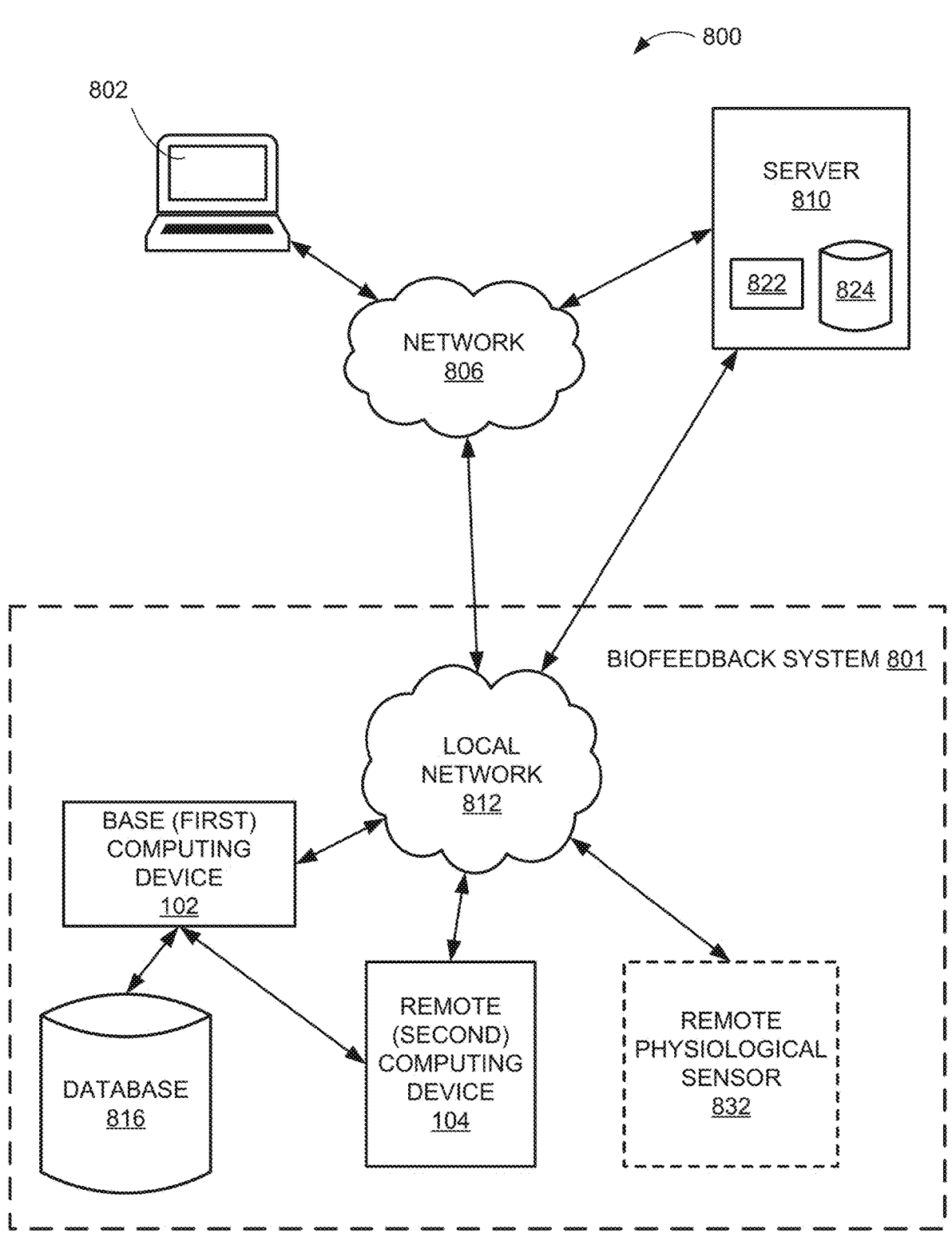
FIG. 8 is an example system block diagram of a system used to guide resonance breathing, according to an implementation of the disclosed technology.

FIG. 6 is a block diagram of an example base computing device 102, according to an example implementation of the disclosed technology. User device 802 and server 810, as depicted in FIG. 8 and described below, may have a similar structure and components that are similar to those described with respect to example base computing device 102 shown in FIG. 6. As shown, base computing device 102 may include a processor 610, an input/output (I/O) device 670, a memory 630 containing an operating system (OS) 640 and a program 650. In some embodiments, program 650 may include an machine learning model (MLM) 652 that may be trained, for example, determining breathing patterns and/or dynamic heart rate patterns. In certain implementations, MLM 652 may issue commands in response to processing an event, in accordance with a model that may be continuously or intermittently updated. Moreover, processor 610 may execute one or more programs (such as via a rules-based platform or the trained MLM 652), that, when executed, perform functions related to disclosed embodiments.

In certain example implementations, base computing device 102 may be a single computing device or may be configured as a distributed computer system including multiple servers or computers that interoperate to perform one or more of the processes and functionalities associated with the disclosed embodiments. In some embodiments, base computing device 102 may leverage one or more servers (e.g., server 810) or one or more servers from a serverless or scaling server system. In some embodiments, the base computing device 102 may further include a peripheral interface, a transceiver 608, a mobile network interface in communication with the processor 610, a bus configured to facilitate communication between the various components of the base computing system 102, and a power source configured associated with power cord 110 to power one or more components of the base computing device 102. In some embodiments, one or more servers 810 may cause base computing device 102 and first computing device to update software (e.g., firmware updates) or updates to the methods 400a, 400b, 400c, 400d.

A peripheral interface, for example, may include the hardware, firmware and/or software that enable(s) communication with various peripheral devices, such as media drives (e.g., magnetic disk, solid state, or optical disk drives), other processing devices, or any other input source used in connection with the disclosed technology. In some embodiments, a peripheral interface may include a serial port, a parallel port, a general-purpose input and output (GPIO) port, a game port, a universal serial bus (USB), a micro-USB port, a USB-C port, a high-definition multimedia interface (HDMI) port, a video port, an audio port, a Bluetooth™ port, a near-field communication (NFC) port, another like communication interface, or any combination thereof.

In some embodiments, a transceiver 608 may be configured to communicate with compatible devices and ID tags when they are within a predetermined range. A transceiver may be compatible with one or more of: radio-frequency identification (RFID), NFC, Bluetooth™, low-energy Bluetooth™ (BLE), WiFi™, ZigBee™, ambient backscatter communications (ABC) protocols or similar technologies.

A mobile network interface may provide access to a cellular network, the Internet, or another wide-area or local area network. In some embodiments, a mobile network interface may include hardware, firmware, and/or software that allow(s) the processor(s) 610 to communicate with other devices via wired or wireless networks, whether local or wide area, private or public, as known in the art. A power source may be configured to provide an appropriate alternating current (AC) or direct current (DC) to power components.

The processor 610 may include one or more of a microprocessor, microcontroller, digital signal processor, co-processor or the like or combinations thereof capable of executing stored instructions and operating upon stored data. The memory 630 may include, in some implementations, one or more suitable types of memory (e.g. such as volatile or non-volatile memory, random access memory (RAM), read only memory (ROM), programmable read-only memory (PROM), erasable programmable read-only memory (EPROM), electrically erasable programmable read-only memory (EEPROM), magnetic disks, optical disks, floppy disks, hard disks, removable cartridges, flash memory, a redundant array of independent disks (RAID), and the like), for storing files including an operating system, application programs (including, for example, a web browser application, a widget or gadget engine, and or other applications, as necessary), executable instructions and data. In one embodiment, the processing techniques described herein may be implemented as a combination of executable instructions and data stored within the memory 630.

The processor 610 may be one or more known processing devices, such as, but not limited to, a microprocessor from the Core™ family manufactured by Intel™, the Ryzen™ family manufactured by AMD™, or a system-on-chip processor using an ARM™ or other similar architecture. The processor 610 may constitute a single core or multiple core processor that executes parallel processes simultaneously, a central processing unit (CPU), an accelerated processing unit (APU), a graphics processing unit (GPU), a microcontroller, a digital signal processor (DSP), a field-programmable gate array (FPGA), an application-specific integrated circuit (ASIC) or another type of processing component. For example, the processor 610 may be a single core processor that is configured with virtual processing technologies. In certain embodiments, the processor 610 may use logical processors to simultaneously execute and control multiple processes. The processor 610 may implement virtual machine (VM) technologies, or other similar known technologies to provide the ability to execute, control, run, manipulate, store, etc. multiple software processes, applications, programs, etc. One of ordinary skill in the art would understand that other types of processor arrangements could be implemented that provide for the capabilities disclosed herein.

In accordance with certain example implementations of the disclosed technology, base computing device 102 may include one or more storage devices configured to store information used by the processor 610 (or other components) to perform certain functions related to the disclosed embodiments. In one example, the base computing device 102 may include the memory 630 that includes instructions to enable the processor 610 to execute one or more applications, such as server applications, network communication processes, and any other type of application or software known to be available on computer systems. Alternatively, the instructions, application programs, etc. may be stored in an external storage or available from a memory over a network. The one or more storage devices may be a volatile or non-volatile, magnetic, semiconductor, tape, optical, removable, non-removable, or other type of storage device or tangible computer-readable medium.

Base computing device 102 may include a memory 630 that includes instructions that, when executed by the processor 610, perform one or more processes consistent with the functionalities disclosed herein. Methods, systems, and articles of manufacture consistent with disclosed embodiments are not limited to separate programs or computers configured to perform dedicated tasks. For example, the base computing device 102 may include the memory 630 that may include one or more programs 650 to perform one or more functions of the disclosed embodiments. For example, in some embodiments, the base computing device 102 may additionally manage dialogue and/or other interactions with the customer via a program 350.

The processor 610 may execute one or more programs 650 located remotely from the base computing device 102. For example, the base computing device 102 may access one or more remote programs (e.g., programs residing with server 810 or second computing device 104) that, when executed, perform functions related to disclosed embodiments.

The memory 630 may include one or more memory devices that store data and instructions used to perform one or more features of the disclosed embodiments. The memory 630 may also include any combination of one or more databases controlled by memory controller devices (e.g., server(s), etc.) or software, such as document management systems, Microsoft™ SQL databases, SharePoint™ databases, Oracle™ databases, Sybase™ databases, or other relational or non-relational databases. The memory 630 may include software components that, when executed by the processor 610, perform one or more processes consistent with the disclosed embodiments. In some embodiments, the memory 630 may include a resonance breathing database 660 for storing related data to enable the base computing device 102 to perform one or more of the processes and functionalities associated with the disclosed embodiments.

The resonance breathing database 660 may include stored data relating to heart rate and interbeat interval data. According to some embodiments, the functions provided by the user resonance breathing database 660 may also be provided by a database that is external to the base computing device 102, such as the database 816 as shown in FIG. 8, or server database 824.

The base computing device 102 may also be communicatively connected to one or more memory devices (e.g., databases) locally or through a network. The remote memory devices may be configured to store information and may be accessed and/or managed by the base communication device. By way of example, the remote memory devices may be document management systems, Microsoft™ SQL database, SharePoint™ databases, Oracle™ databases, Sybase™ databases, or other relational or non-relational databases. Systems and methods consistent with disclosed embodiments, however, are not limited to separate databases or even to the use of a database.

The base computing device 102 may also include one or more I/O devices 670 that may comprise one or more interfaces for receiving signals or input from devices and providing signals or output to one or more devices that allow data to be received and/or transmitted by the base computing device 102. For example, base computing device 102 may include interface components, which may provide interfaces to one or more input devices, such as one or more keyboards, touch screens, digital cameras, microphones, sensors, buttons, and the like, that enable the base computing device 102 to receive data from a user (such as, for example, via user input buttons 114a, 114b (see FIG. 1D) or user device 802).

Base computing device 102 may also include a display 106. Display 106 may be one or more displays such as one or more organic light emitting display (OLED) displays, one or more micro light emitting diode displays, one or more liquid crystal displays (LCD), or similar displays. In some embodiments, display 106 may include a first display 106a including a plurality of lights that art vertically stacked. For example, first display 106a may include about 4 to about 50 (e.g., 14) vertically stacked ring-shaped LED lights as shown in FIGS. 1B and 1F as 128a-128n. First display 106a is configured to indicate when resonance breathing is achieved based on interbeat interval data. Display 106 may include a second display 106b of one of the previously mentioned displays or LED display configured to indicate in instantaneous heart rate.

Base computing device 102 may also include an audio output device or speaker 118 configured to output an audio content to quickly guide a user to resonance breathing. In some embodiments, the speaker 118 may be omitted or muted when a user connects an exterior audio source via a wired or wireless connection (e.g., wireless headphones).

Base computing device 102 may include induction charging coils 105 and related circuits to enable induction charging between base computing device 102 and second computing device 104. Induction charging coils 105 may include a switch or sensor to detect when second computing device 104 is connected and placed into the correct position in cradle 102c (see FIG. 1F).

In examples of the disclosed technology, the base computing device 102 may include any number of hardware and/or software applications that are executed to facilitate any of the operations. The one or more I/O interfaces may be utilized to receive or collect data and/or user instructions from a wide variety of input devices. Received data may be processed by one or more computer processors as desired in various implementations of the disclosed technology and/or stored in one or more memory devices.

Base computing device 102 may contain programs that train, implement, store, receive, retrieve, and/or transmit one or more MLMs. Machine learning models may include a neural network model, a generative adversarial model (GAN), a recurrent neural network (RNN) model, a deep learning model (e.g., a long short-term memory (LSTM) model), a random forest model, a convolutional neural network (CNN) model, a support vector machine (SVM) model, logistic regression, XGBoost, and/or another machine learning model. Models may include an ensemble model (e.g., a model comprised of a plurality of models). In some embodiments, training of a model may terminate when a training criterion is satisfied. Training criterion may include a number of epochs, a training time, a performance metric (e.g., an estimate of accuracy in reproducing test data), or the like. The base computing device 102 may be configured to adjust model parameters during training. Model parameters may include weights, coefficients, offsets, or the like. Training may be supervised or unsupervised.

The base computing device may be configured to train machine learning models by optimizing model parameters and/or hyperparameters (hyperparameter tuning) using an optimization technique, consistent with disclosed embodiments. Hyperparameters may include training hyperparameters, which may affect how training of the model occurs, or architectural hyperparameters, which may affect the structure of the model. An optimization technique may include a grid search, a random search, a gaussian process, a Bayesian process, a Covariance Matrix Adaptation Evolution Strategy (CMA-ES), a derivative-based search, a stochastic hill-climb, a neighborhood search, an adaptive random search, or the like. Base computing device 102 may be configured to optimize statistical models using known optimization techniques.

Furthermore, the base computing device 102 may include programs configured to retrieve, store, and/or analyze properties of data models and datasets. For example, base computing device 102 may include or be configured to implement one or more data-profiling models. A data-profiling model may include machine learning models and statistical models to determine the data schema and/or a statistical profile of a dataset (e.g., to profile a dataset), consistent with disclosed embodiments. A data-profiling model may include an RNN model, a CNN model, or other machine-learning model.

Base computing device 102 may include algorithms to determine a data type, key-value pairs, row-column data structure, statistical distributions of information such as keys or values, or other property of a data schema may be configured to return a statistical profile of a dataset (e.g., using a data-profiling model). Base computing device 102 may be configured to implement univariate and multivariate statistical methods. Base computing device 102 may include a regression model, a Bayesian model, a statistical model, a linear discriminant analysis model, or other classification model configured to determine one or more descriptive metrics of a dataset. For example, base computing device 102 may include algorithms to determine an average, a mean, a standard deviation, a quantile, a quartile, a probability distribution function, a range, a moment, a variance, a covariance, a covariance matrix, a dimension and/or dimensional relationship (e.g., as produced by dimensional analysis such as length, time, rate, mass, etc.) or any other descriptive metric of a dataset.

Base computing device 102 may be configured to return a statistical profile of a dataset (e.g., using a data-profiling model or other model). A statistical profile may include a plurality of descriptive metrics. For example, the statistical profile may include an average, a mean, a standard deviation, a range, a moment, a variance, a covariance, a covariance matrix, a similarity metric, or any other statistical metric of the selected dataset. In some embodiments, base computing device 102 may be configured to generate a similarity metric representing a measure of similarity between data in a dataset. A similarity metric may be based on a correlation, covariance matrix, a variance, a frequency of overlapping values, or other measure of statistical similarity.

Base computing device 102 may be configured to generate a similarity metric based on data model output, including data model output representing a property of the data model. For example, base computing device 102 may be configured to generate a similarity metric based on activation function values, embedding layer structure and/or outputs, convolution results, entropy, loss functions, model training data, or other data model output). For example, a synthetic data model may produce first data model output based on a first dataset and a produce data model output based on a second dataset, and a similarity metric may be based on a measure of similarity between the first data model output and the second-data model output. In some embodiments, the similarity metric may be based on a correlation, a covariance, a mean, a regression result, or other similarity between a first data model output and a second data model output. Data model output may include any data model output as described herein or any other data model output (e.g., activation function values, entropy, loss functions, model training data, or other data model output). In some embodiments, the similarity metric may be based on data model output from a subset of model layers. For example, the similarity metric may be based on data model output from a model layer after model input layers or after model embedding layers. As another example, the similarity metric may be based on data model output from the last layer or layers of a model.

Base computing device 102 may be configured to classify a dataset. Classifying a dataset may include determining whether a dataset is related to another datasets. Classifying a dataset may include clustering datasets and generating information indicating whether a dataset belongs to a cluster of datasets. In some embodiments, classifying a dataset may include generating data describing the dataset (e.g., a dataset index), including metadata, an indicator of whether data element includes actual data and/or synthetic data, a data schema, a statistical profile, a relationship between the test dataset and one or more reference datasets (e.g., node and edge data), and/or other descriptive information. Edge data may be based on a similarity metric. Edge data may indicate a similarity between datasets and/or a hierarchical relationship (e.g., a data lineage, a parent-child relationship). In some embodiments, classifying a dataset may include generating graphical data, such as anode diagram, a tree diagram, or a vector diagram of datasets. Classifying a dataset may include estimating a likelihood that a dataset relates to another dataset, the likelihood being based on the similarity metric.

Base computing device 102 may include one or more data classification models to classify datasets based on the data schema, statistical profile, and/or edges. A data classification model may include a convolutional neural network, a random forest model, a recurrent neural network model, a support vector machine model, or another machine learning model. A data classification model may be configured to classify data elements as actual data, synthetic data, related data, or any other data category. In some embodiments, base computing device 102 is configured to generate and/or train a classification model to classify a dataset, consistent with disclosed embodiments.

Base computing device 102 may also contain one or more prediction models. Prediction models may include statistical algorithms that are used to determine the probability of an outcome, given a set amount of input data. For example, prediction models may include regression models that estimate the relationships among input and output variables. Prediction models may also sort elements of a dataset using one or more classifiers to determine the probability of a specific outcome. Prediction models may be parametric, non-parametric, and/or semi-parametric models.

In some examples, prediction models may cluster points of data in functional groups such as "random forests." Random Forests may comprise combinations of decision tree predictors. (Decision trees may comprise a data structure mapping observations about something, in the "branch" of the tree, to conclusions about that thing's target value, in the "leaves" of the tree.) Each tree may depend on the values of a random vector sampled independently and with the same distribution for all trees in the forest. Prediction models may also include artificial neural networks. Artificial neural networks may model input/output relationships of variables and parameters by generating a number of interconnected nodes which contain an activation function. The activation function of a node may define a resulting output of that node given an argument or a set of arguments. Artificial neural networks may generate patterns to the network via an 'input layer', which communicates to one or more "hidden layers" where the system determines regressions via weighted connections. Prediction models may additionally or alternatively include classification and regression trees, or other types of models known to those skilled in the art. To generate prediction models, the asset detection system may analyze information applying machine-learning methods.

While base computing device 102 has been described as one form for implementing the techniques described herein, other, functionally equivalent, techniques may be employed. For example, some or all of the functionality implemented via executable instructions may also be implemented using firmware and/or hardware devices such as application specific integrated circuits (ASICs), programmable logic arrays, state machines, etc. Furthermore, other implementations of base computing device 102 may include a greater or lesser number of components than those illustrated.

Figure 7:
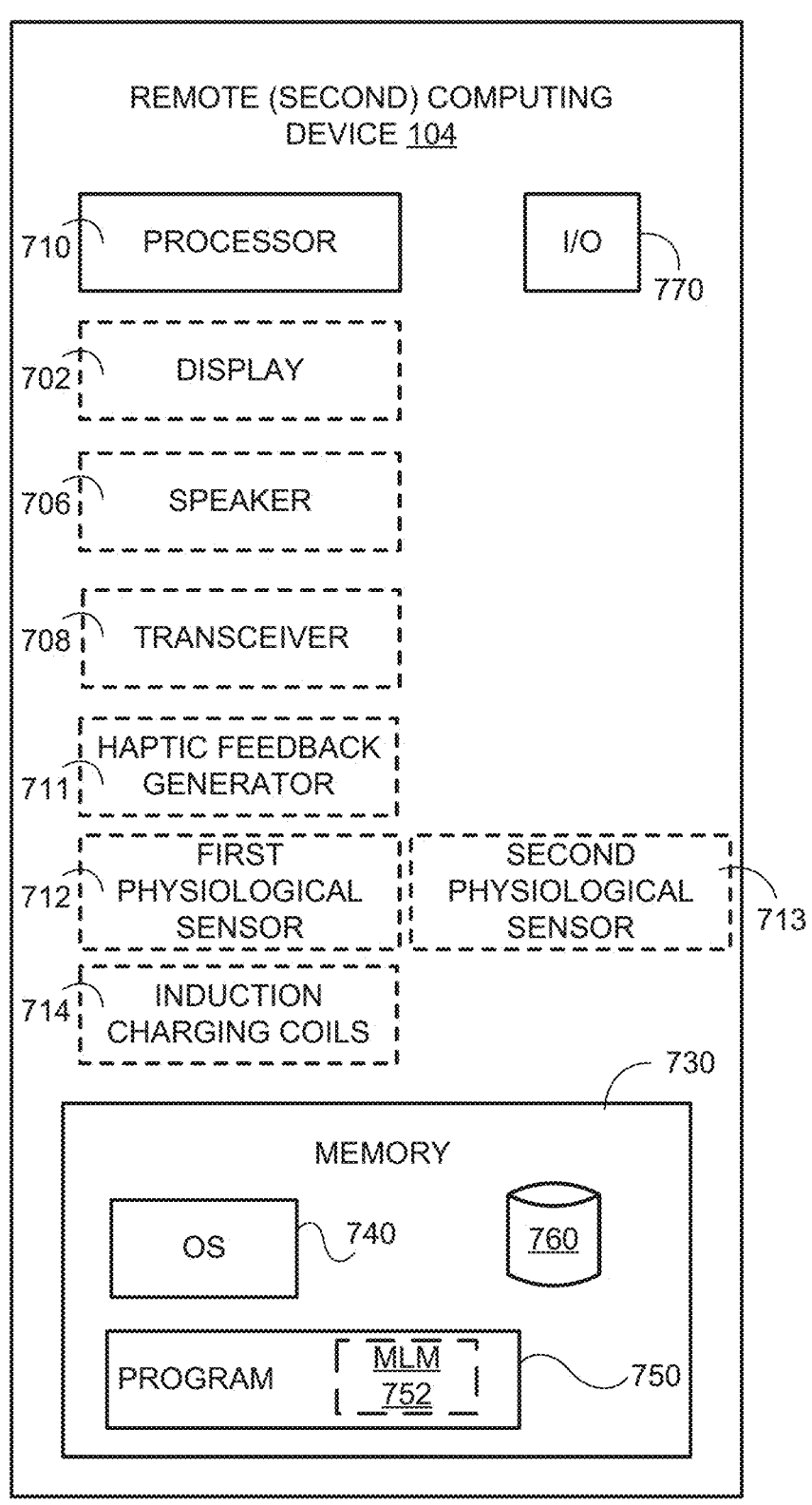
FIG. 7 is a block diagram of an example first computing device, according to an example implementation of the disclosed technology.

FIG. 7 is a block diagram of an example second computing device 104, according to an example implementation of the disclosed technology. Similar to base computing device 102, second computing device 104 may include a processor 710, an input/output device ("I/O") 770, display 702, audio output device or speaker 706, optional transceiver 708, and memory 730. These components are similar to those components discussed above corresponding to processor 610, display 126, speaker 118, transceiver 608, I/O device 670, and memory 630. Thus, these components will not be described again for brevity. However, second computing device 104 include may also include an optional haptic feedback generator 711, one or more optional first physiological sensors 712 such as a heart rate sensor (e.g., the PPG sensor 146), one or more optional second physiological sensors 713 and optional induction charging coils 714. Second computing device 104 may communicate wirelessly or via a wired connection with base computing device 102. Some non-limiting examples of first or second physiological sensors 712, 713 to generate physiological data used in feedback determinations may include a palm temperature sensor (e.g., via in the form of a copper ring similar to strain gauge 144 as shown in FIG. 1H), a skin conductance sensor, a non-invasive blood pressure sensor (e.g., strain gauge 144 as shown in FIG. 1H), a musculoskeletal sensor, an oxygen saturation (SpO2) sensor, a capnometer, a cortisol sensor, a electroencephalogram (EEG) sensor, an electromyogram (EMG) sensor, the photoplethysmography (PPG) sensor 146, a pressure sensor, and a breathing rate sensor (e.g., Tidal volume sensor).

Second computing device 104 may include also include a haptic feedback generator 711 configured to generate a dynamic feedback pattern corresponding to a breathing pattern or mirroring a user's instantaneous heart rate. The haptic feedback generator 711 may generate any number of feedback patterns.

Second computing device 104 may include one or more physiological sensors such as a photoplethysmography (PPG) sensor 146 and/or other heart rate sensor configured to instantaneously detect a user's heart rate or a user's pulse wave characteristic when second computing device 104 is place in the palm of their hand. Alternatively, second computing device 104 could be watch or other wearable device and detect a heart rate at a wrist, check, finger, or other area. In some embodiments, the physiological sensor, such as the PPG sensor 146, may include a plurality of lights (e.g., light emitting diodes) and a plurality of reflectors with the lights spread apart by at least a first distance to prevent interference between reflectors. In some embodiments the PPG sensor 146 may be configured to decrease transmission frequency (e.g., transmit data every 2 seconds, 3 seconds, 4 seconds, 5 seconds, 6 seconds, 7 second, 8 seconds, 9 seconds, or 10 seconds) to conserve battery life of the PPG sensor 146 or may increase transmission frequency (e.g., every 0.25 seconds, 0.5 seconds, 1 second, 2 seconds, 3 seconds, 4 seconds, 5 seconds, 6 seconds, 7 second, 8 seconds, or 9 seconds) during periods of rapid change in a user's interbeat interval measurements to increase accuracy of the PPG sensor 146.

Second computing device 104 may also include induction charging coils 714 that correspond to induction charging coils 105 to provide charging to one or more batteries (not shown) of second computing device 104.

FIG. 8 is a block diagram of an example system that may be used to view and interact with biofeedback system 801, according to an example implementation of the disclosed technology. The components and arrangements shown in FIG. 8 are not intended to limit the disclosed embodiments as the components used to implement the disclosed processes and features may vary. As shown, base computing device 102 may interact with a user device 802 via a network 806. In certain example implementations, biofeedback system 701 may include a local network 812, the base computing device 102, a database 816 (internal or external to base computing device 102), and the second computing device 104.

In some embodiments, biofeedback system 801 may include base computing device 102 in the form of any mobile computing device such as a smart phone or a wearable smart device and second computing device 104 in the form of a pair of headphones that may include the instantaneous heart rate sensor described above (e.g., PPG sensor 146). The second computing device 104 in these examples would communicate with the base computing device 102 to provide instantaneous heart rate data to base computing device 102 and base computing device 102 would communicate with second computing device 104 to provide audio feedback (e.g., default/custom breathing pacer and indication on progress).

In some embodiments, biofeedback system 801 includes a remote physiological sensor 832 (e.g., chest strap with instantaneous heart rate sensor such as a PPG sensor) that connects with base computing device 102 or second computing device 104. Headphones may be used to aid a user in falling asleep or during running or other exercises. In some embodiments, only headphones are used as the second computing device 104, which performs all the calculations and processing.

In some embodiments, a respective user may operate the user device 802. The user device 802 can include one or more of a mobile device, smart phone, general purpose computer, tablet computer, laptop computer, smart wearable device, voice command device, other mobile computing device, or any other device capable of communicating with the network 806 and ultimately communicating with one or more components of the biofeedback system 501.

According to some embodiments, the user device 802 may include an environmental sensor for obtaining audio or visual data, such as a microphone and/or digital camera, a geographic location sensor for determining the location of the device, an input/output device such as a transceiver for sending and receiving data, a display for displaying digital images, one or more processors, and a memory in communication with the one or more processors.

Base computing device 102 may include programs functions, algorithms) to configure data for visualizations and provide visualizations of datasets and data models on the user device 802. This may include programs to generate graphs and display graphs. Base computing device 102 may include programs to generate histograms, scatter plots, time series, or the like on the user device 802. Base computing device 102 may also be configured to display properties of data models and data model training results including, for example, architecture, loss functions, cross entropy, activation function values, embedding layer structure and/or outputs, convolution results, node outputs, or the like on the user device 802.

The network 806 may be of any suitable type, including individual connections via the internet such as cellular or WiFi™ networks. In some embodiments, the network 806 may connect terminals, services, and mobile devices using direct connections such as RFID, NFC, Bluetooth™, Bluetooth Low Energy (BLE), WiFi™, ZigBee™, ABC protocols, universal serial bus (USB), wide area network (WAN), or local area network (LAN). Because the information transmitted may be personal or confidential, security concerns may dictate one or more of these types of connections be encrypted or otherwise secured. In some embodiments, however, the information being transmitted may be less personal, and therefore the network connections may be selected for convenience over security.

The network 806 may include any type of computer networking arrangement used to exchange data. For example, the network 806 may be the Internet, a private data network, virtual private network (VPN) using a public network, and/or other suitable connection(s) that enable(s) components in the system 800 environment to send and receive information between the components of the system 800. The network 806 may also include a PSTN and/or a wireless network.

Server 810 may include a computer system configured to carry out any of the functions associated with base computing device 102 or second computing device 104. Server 810 may include any number of the components described with respect of base computing device 102. For example, server 810 include one or more processors 822 and memory or server database 824.

The local network 812 may include any type of computer networking arrangement used to exchange data in a localized area, such as WiFi™, Bluetooth™, Ethernet, and other suitable network connections that enable components of the biofeedback system 801 to interact with one another and to connect to the network 806 for interacting with components in the system 800 environment. In some embodiments, the local network 812 may include an interface for communicating with or linking to the network 806. In other embodiments, certain components of biofeedback system 801 may communicate directly without a separate local network 806.

The biofeedback system 801 may be hosted in a cloud computing environment (not shown). The cloud computing environment may provide software, data access, data storage, and computation. Furthermore, the cloud computing environment may include resources such as applications (apps), VMs, virtualized storage (VS), or hypervisors (HYP). User device 802 may be able to access biofeedback system 801 using the cloud computing environment. User device 802 may be able to access biofeedback system 801 using specialized software. The cloud computing environment may eliminate the need to install specialized software on user device 802.

In accordance with certain example implementations of the disclosed technology, biofeedback system 801 may include one or more computer systems configured to compile data from a plurality of sources such as base computing device 102, server 810, second computing device 104, database 816, and/or user device 802. Base computing device 102 may receive, analyze, and dynamically change audio, visual, or haptic feedback to quickly guide a user to resonance breathing. According to some embodiments, database 816 may also serve as a back-up storage device and may contain data and information that is also stored on, for example, resonance breathing database 660, as discussed with reference to FIG. 6.

Embodiments consistent with the present disclosure may include datasets. Datasets may comprise actual data reflecting real-world conditions, events, and/or measurements. However, in some embodiments, disclosed systems and methods may fully or partially involve synthetic data (e.g., anonymized actual data or fake data). Datasets may involve numeric data, text data, and/or image data. For example, datasets may include transaction data, financial data, demographic data, public data, government data, environmental data, traffic data, network data, transcripts of video data, genomic data, proteomic data, and/or other data. Datasets of the embodiments may be in a variety of data formats including, but not limited to, PARQUET, AVRO, SQLITE, POSTGRESQL, MYSQL, ORACLE, HADOOP, CSV, JSON, PDF, JPG, BMP, and/or other data formats.

Datasets of disclosed embodiments may have a respective data schema (e.g., structure), including a data type, key-value pair, label, metadata, field, relationship, view, index, package, procedure, function, trigger, sequence, synonym, link, directory, queue, or the like. Datasets of the embodiments may contain foreign keys, for example, data elements that appear in multiple datasets and may be used to cross-reference data and determine relationships between datasets. Foreign keys may be unique (e.g., a personal identifier) or shared (e.g., a postal code). Datasets of the embodiments may be "clustered," for example, a group of datasets may share common features, such as overlapping data, shared statistical properties, or the like. Clustered datasets may share hierarchical relationships (e.g., data lineage).

Example Use Case

The following example use case describes an example of a typical user flow pattern. This section is intended solely for explanatory purposes and not in limitation.

In one example, James may walk up to a base computing device 102 shaped like a lamp and picks up a puck or round stone-shaped second computing device 104. Once James picks up the second computing device 104, the second computing device 104 wakes up and the base computing device 102 detects that the second computing device 104 was removed away from induction charging coils 105 and outputs a default breathing pattern via integrated speakers 118.

The second computing device 104 detects James' interbeat interval (IBI) via first physiological sensor 712 (e.g., the PPG sensor 146) and begins continuously or dynamically transmitting interbeat interval data associated with James' heart rate to base computing device 102 via a short-range wireless communication pathway (e.g., Bluetooth Low Energy). Base computing device 102 may display James' instantaneous heart rate on display 106b. Base computing device 102 extracts one or more characteristics from the interbeat interval data such as instantaneous heart rate, change in heart rate, minimum and maximum interbeat interval values (e.g., troughs and peaks in data), and/or frequencies of peak and troughs. Based on one or more of these characteristics and a determined light position, base computing device 102 may light up one or more lights 128a-128n of its fourteen vertically stacked ring-shaped LED lights in order from lowest to highest.

For example, base computing device 102 may determine a first peak amplitude of 3 and turn on lights 128n, 128m, and 128l at a first rate about 2 seconds in the color blue. Base computing device 102 may next determine a first trough amplitude of −3 and turn off lights in order from 128l, 128m, and 128n at a rate of about 2.07 seconds based on a difference in amplitude of heart rate changes. Base computing device 102 may next determine a second peak amplitude of 4 and turn on lights 128n, 128m, 128l, 128k at a first rate about 1.96 seconds in the color blue. However, if base computing device 102 determines that a trough amplitude causes the display position to be less than zero, base computing device 102 will round the display position to zero while preserving a time interval associated with the peak to trough heart rate change.

In addition, base computing device 102 may dynamically determine a second breathing pattern based on the one or more characteristics. Once base computing device 102 determines that a number (e.g., 10 immediately previous) maximum and minimum interbeat interval values are within a threshold range (e.g., 4.5 to 7.5 cycles per minute), base computing device 102 may change the color of the lights of first display 106a from blue to green to indicate the user has achieved resonance breathing. This color may be maintained until base computing device 102 detects second computing device 104 in range of its induction charging coils 105 or when the frequencies associated with James' heart rate changes or no longer meets the threshold.

In another similar example, James may walk up to a base computing device 102 shaped like a lamp and picks up a puck or round stone-shaped second computing device 104. Once James picks up or moves the second computing device 104, the second computing device 104 wakes up and detects that the second computing device 104 was removed away from induction charging coils 105 or otherwise moved and causes a default breathing pattern to be output via speakers 118 integrated into base computing device 102.

The second computing device 104 detects James' interbeat interval (IBI) via first physiological sensor 712 (e.g., the PPG sensor 146) and begins continuously or dynamically transmitting interbeat interval data associated with James' heart rate to base computing device 102 via a short-range wireless communication pathway (e.g., Bluetooth Low Energy). Base computing device 102 may display James' instantaneous heart rate on display 106b. Second computing device 104 extracts one or more characteristics from the interbeat interval data such as instantaneous heart rate, change in heart rate, minimum and maximum interbeat interval values (e.g., troughs and peaks in data), and/or frequencies of peak and troughs. Based on one or more of these characteristics and a determined light position, second computing device 104 causes base computing device 102 to light up one or more lights 128a-128n of its fourteen vertically stacked ring-shaped LED lights in order from lowest to highest.

For example, second computing device 104 may determine a first peak amplitude of 3 and cause lights 128n, 128*m*, and 128*l* on base computing device 102 to turn on at a first rate about 2 seconds in the color blue. Second computing device 104 may next determine a first trough amplitude of −3 and cause lights 128*l*, 128*m*, and 128*n* of base computing device to turn off in order at a rate of about 2.07 seconds based on a difference in amplitude of heart rate changes. Second computing device 104 may next determine a second peak amplitude of 4 and cause lights 128*n*, 128*m*, 128*l*, 128*k* of base computing device 102 to turn on at a first rate about 1.96 seconds in the color blue. However, if second computing device 104 determines that a trough amplitude causes the display position to be less than zero, Second computing device 104 will round the display position to zero while preserving a time interval associated with the peak to trough heart rate change.

In addition, second computing device 104 may dynamically determine a second breathing pattern based on the one or more characteristics. Once base computing device 102 determines that a number (e.g., 10 immediately previous) maximum and minimum interbeat interval values are within a threshold range (e.g., 4.5 to 7.5 cycles per minute), second computing device 104 may cause base computing device 102 to change the color of the lights of first display 106*a* from blue to green to indicate the user has achieved resonance breathing. This color may be maintained until second computing device 104 is in range of induction charging coils 105 or when the frequencies associated with James' heart rate changes or no longer meets the threshold.

In some examples, disclosed systems or methods may involve one or more of the following clauses:

Clause 1: A system for dynamically guiding heart rate variability feedback, the system comprising: a remote computing device comprising a heart rate sensor; a base computing device comprising: an audio output device; a display; one or more processors; and a memory having stored thereon computer program code that, when executed by the one or more processors, is configured to cause the one or more processors to: receive user input via the remote computing device or the base computing device; responsive to receiving the user input, output an audio content associated with a default breathing pattern via the audio output device; dynamically receive interbeat interval data from the heart rate sensor; dynamically extract one or more characteristics from the interbeat interval data; cause the display to indicate a dynamic visual pattern based on the one or more characteristics; dynamically determine a second breathing pattern based on the one or more characteristics; and dynamically change the audio pattern based on the second breathing pattern.

Clause 2: The system of clause 1, wherein the computer program code is further configured to cause the one or more processors to: determine maximum and minimum interbeat interval values from the interbeat interval data; determine whether a threshold number of maximum and minimum interbeat interval values correspond to a first frequency band; responsive to determining that the threshold number of maximum and minimum interbeat interval values are in the first frequency band, indicate that the threshold number of maximum and minimum interbeat interval values are in the first frequency band via an audio change, a display change, a visual, a haptic feedback change, or a combination thereof.

Clause 3: The system of clause 1, wherein the heart rate variability pattern is displayed in a first color.

Clause 4: The system of any of clauses 1 to 3, wherein the computer program code is further configured to cause the one or more processors to: determine whether a threshold number of interbeat intervals corresponds to a first frequency band; responsive to determining that the threshold number of interbeat intervals corresponds to the first frequency band, display the heart rate variability pattern in a second color that is different from the first color.

Clause 5: The system of any of clauses 1 to 4, wherein the computer program code is further configured to cause the one or more processors to: cause a portion of the display to display an instantaneous heart rate.

Clause 6: The system of any of clauses 1 to 5, wherein the one or more characteristics comprise a heart rate, a heart rate change, peak-trough amplitude, and peak-trough frequencies, or combinations thereof.

Clause 7: The system of clause 6, wherein the indication of the heart rate variability pattern dynamically changes based on characteristics of peak-trough frequencies.

Clause 8: The system of any of clauses 1 to 6, wherein the remote computing device comprises a haptic feedback device configured to provide a haptic feedback pattern corresponding to the interbeat interval or corresponding to the audio pattern or the dynamic visual pattern.

Clause 9: The system of clause 6, wherein the remote computing device further comprises a haptic feedback device configured to generate a haptic feedback pattern corresponding to the default breathing pattern or the second breathing pattern which correspond to different inhale-exhale progress curves plotting diaphragm expansion percentage against time.

Clause 10: The system of clause 9, wherein the computer program code is further configured to cause the one or more processors to cause the haptic feedback device to change haptic feedback intensity associated with the default breathing pattern or second breathing pattern in response determining the diaphragm expansion percentage changes by a threshold diaphragm expansion percentage.

Clause 11: The system of clause 10, wherein the change in haptic feedback intensity during an inhale portion of the default breathing pattern or the second breathing pattern correspond with increases in intensity until the diaphragm expansion percentage reaches a first threshold.

Clause 12: The system of clause 10, wherein the change in haptic feedback intensity during an exhale portion of the default breathing pattern or second breathing pattern correspond with increases in intensity until the diaphragm expansion percentage reaches a second threshold.

Clause 13: The system of clause 1, wherein the default breathing pattern and the second breathing pattern corresponds to different inhale-exhale progress curves plotting diaphragm expansion percentage against time.

Clause 14: The system of clause 13, wherein the computer program code is further configured to cause the one or more processors to trigger a change in volume of the audio output associated with the default breathing pattern or second breathing pattern in response to determining that the diaphragm expansion percentage changed by a threshold diaphragm expansion percentage.

Clause 15: The system of clause 14, wherein the change in volume of the audio output during an inhale portion of the default breathing pattern or the second breathing pattern correspond with increases in volume until the diaphragm expansion percentage reaches a first threshold and then corresponds with decreases in volume until the diaphragm expansion percentage reaches a second threshold.

Clause 16: The system of clause 14, wherein the volume change during an exhale portion of the default breathing pattern or second breathing pattern correspond with increases in volume until the diaphragm expansion percentage reaches a third threshold and then corresponds with decreases in volume until the diaphragm expansion percentage reaches a fourth threshold.

Clause 17: The system of clause 1, wherein: the remote computing device comprises a strain gauge configured to measure blood pressure when a user holds the remote computing device with a first grip releasing to a second grip, and the computer program code is further configured to cause the one or more processors of the base computing device to receive blood pressure data from the remote computing device and update the default breathing pattern or second breathing pattern based on the blood pressure data.

Clause 18: A base computing device, comprising: one or more processors; and a memory having stored thereon computer program code that, when executed by the one or more processors, is configured to cause the one or more processors to: dynamically receive interbeat interval data from an instantaneous heart rate sensor, wherein the interbeat interval data comprises one or more interbeat intervals; output an audio content associated with a default breathing pattern via an audio output device; dynamically extract one or more characteristics from the interbeat interval data in real time; dynamically determine a second breathing pattern based on the on the one or more characteristics; and dynamically change the audio content based on the second breathing pattern.

Clause 19: The base computing device of clause 18, wherein the default breathing pattern and the second breathing pattern corresponds to different inhale-exhale progress curves plotting diaphragm expansion percentage against time.

Clause 20: The base computing device of clause 19, wherein the computer program code is further configured to cause the one or more processors to trigger a change in volume of the audio content associated with the default breathing pattern or second breathing pattern in response to determining the diaphragm expansion percentage changed by a threshold diaphragm expansion percentage.

Clause 21: The base computing device of clause 20, wherein the change in volume during an inhale portion of the default breathing pattern or the second breathing pattern correspond with increases in volume until the diaphragm expansion percentage reaches a first threshold and then corresponds with decreases in volume until the diaphragm expansion percentage reaches a second threshold.

Clause 22: The base computing device of clause 20, wherein the change in volume during an exhale portion of the default breathing pattern or second breathing pattern correspond with increases in volume until the diaphragm expansion percentage reaches a third threshold and then corresponds with decreases in volume until the diaphragm expansion percentage reaches fourth threshold.

Clause 23: The base computing device of clause 18, wherein the computer program code is further configured to cause the one or more processors to: cause a display to dynamically indicate a heart rate variability pattern based on the one or more characteristics.

Clause 24: The base computing device of clause 18 or 19, wherein the computer program code is further configured to cause the one or more processors to: determine whether a threshold number of the one or more interbeat intervals corresponds to a first frequency band; responsive to determining that the threshold number of interbeat intervals corresponds to the first frequency band, indicate that the threshold number of interbeat intervals are in the first frequency band via an audio change, display change, or both.

Clause 25: The base computing device of clause 19, wherein the heart rate variability pattern is displayed in a first color.

Clause 26: The base computing device of clause 20, wherein the computer program code is further configured to cause the one or more processors to: determine whether a threshold number of interbeat intervals are in a first frequency band; responsive to determining that the threshold number of interbeat intervals are in the first frequency band, display the heart rate variability pattern in a second color that is different from the first color.

Clause 27: The base computing device of any of clauses 18 to 26, wherein the computer program code is further configured to cause the one or more processors to: cause the display to display an instantaneous heart rate.

Clause 28: The base computing device of any of clauses 18 to 27, wherein the one or more characteristics comprise frequencies associated with heart rate change.

Clause 29: The system of clause 28, wherein the indication of the heart rate variability pattern dynamically changes based on the frequencies associated with heart rate change.

Clause 30: The system of any of clauses 18 to 29, wherein the audio pattern comprises a series of ascending and descending tones, tones of different volume levels, or both.

Clause 31: A base computing device, comprising: one or more processors; and a memory having stored thereon computer program code that, when executed by the one or more processors, is configured to cause the one or more processors to: dynamically receive interbeat interval data from an instantaneous heart rate sensor, wherein the interbeat interval data comprises one or more interbeat intervals; dynamically extract one or more characteristics from the interbeat interval data; and cause a display to indicate a dynamic heart rate variability pattern based on the one or more characteristics.

Clause 32: The base computing device of clause 31, wherein the display comprises a plurality of lights and the one or more characteristics comprises a frequency of adjacent peaks, troughs, or combinations thereof with respect to heart rate measurements.

Clause 33: The base computing device of clause 31 or 32, wherein indicating the dynamic heart rate variability pattern comprises turning on the plurality of lights in series starting from a lowest positioned light of the plurality of lights.

Clause 34: The base computing device of clause 33, wherein the dynamic heart rate variability pattern comprises turning off the plurality of lights in series starting from a highest positioned light that is turned on of the plurality of lights.

Clause 35: A user input device, comprising: a heart rate sensor; a haptic feedback device; a transceiver; one or more processors; and a memory having stored thereon computer program code that, when executed by the one or more processors, is configured to cause the one or more processors to: dynamically receive interbeat interval data from the heart rate sensor, wherein the interbeat interval data comprises one or more interbeat intervals; dynamically transmit, via the transceiver over a wireless connection, the interbeat interval data to a base computing device; dynamically receive, via the transceiver over the wireless connection, haptic pattern data from the base computing device; and cause the haptic feedback device to generate a dynamic haptic pattern based on the haptic pattern data.

Clause 36: The user input device of clause 35, wherein the computer program code is further configured to cause the one or more processors to cause the haptic feedback device to change haptic feedback intensity associated with the dynamic haptic pattern in response determining the diaphragm expansion percentage changes by a threshold diaphragm expansion percentage.

Clause 37: The user input device of clause 36, wherein the change in haptic feedback intensity during an inhale portion of the dynamic haptic pattern correspond with increases in intensity until the diaphragm expansion percentage reaches a first threshold.

Clause 38: The user input device of clause 37, wherein the change in haptic feedback intensity during an exhale portion of the dynamic haptic pattern correspond with increases in intensity until the diaphragm expansion percentage reaches a second threshold.

Clause 39: The user input device of clause 35, further comprising a strain gauge configured to measure blood pressure when a user holds the user input device with a first grip and releases to a second grip, and wherein the computer program code is further configured to cause the one or more processors of the user input device to transmit the blood pressure data to the base computing device and cause the base computing device to update the default breathing pattern or second breathing pattern based on the blood pressure data.

Clause 40: A user input device, comprising: a heart rate sensor; a haptic feedback device; a transceiver; one or more processors; and a memory having stored thereon computer program code that, when executed by the one or more processors, is configured to cause the one or more processors to: dynamically receive interbeat interval data from the heart rate sensor, wherein the interbeat interval data comprises one or more interbeat intervals; dynamically determine a dynamic haptic pattern; and cause the haptic feedback device to generate the dynamic haptic pattern.

Clause 41: The user input device of clause 40, wherein the computer program code is further configured to cause the one or more processors to cause the haptic feedback device to change haptic feedback intensity associated with the dynamic haptic pattern in response determining the diaphragm expansion percentage changes by a threshold diaphragm expansion percentage.

Clause 42: The user input device of clause 41, wherein the change in haptic feedback intensity during an inhale portion of the dynamic haptic pattern correspond with increases in intensity until the diaphragm expansion percentage reaches a first threshold.

Clause 43: The user input device of clause 41, wherein the change in haptic feedback intensity during an exhale portion of the dynamic haptic pattern correspond with increases in intensity until the diaphragm expansion percentage reaches a second threshold.

Clause 44: The user input device of clause 40, wherein the dynamic haptic pattern comprises one or more ascending intensity patterns and one or more descending intensity patterns.

Clause 45: A base computing device, comprising: an audio output device; a display; a transceiver; one or more processors; and a memory having stored thereon computer program code that, when executed by the one or more processors, is configured to cause the one or more processors to: receive, the transceiver over a wireless connection, interbeat interval data from a user input device, wherein the interbeat interval data comprises one or more interbeat intervals and the user input device comprises an instantaneous hear rate sensor; responsive to receiving, via the transceiver over the wireless connection, the interbeat interval data or receiving user input, output an audio pattern associated with a default breathing pattern from the audio output device; dynamically extract one or more characteristics from the interbeat interval data; cause the display to indicate a heart rate variability pattern based on the one or more characteristics; dynamically determine a second breathing pattern based on the one or more characteristics; and dynamically change the audio pattern based on the second breathing pattern.

Clause 46: The base computing device of clause 45, wherein the default breathing pattern and the second breathing pattern corresponds to different inhale-exhale progress curves plotting diaphragm expansion percentage against time.

Clause 47: The base computing device of clause 46, wherein the computer program code is further configured to cause the one or more processors to trigger a change in volume of the audio content associated with the default breathing pattern or second breathing pattern in response to determining the diaphragm expansion percentage changed by a threshold diaphragm expansion percentage.

Clause 48: The base computing device of clause 46, wherein the change in volume during an inhale portion of the default breathing pattern or the second breathing pattern correspond with increases in volume until the diaphragm expansion percentage reaches a first threshold and then corresponds with decreases in volume until the diaphragm expansion percentage reaches a second threshold.

Clause 49: The base computing device of clause 48, wherein the change in volume during an exhale portion of the default breathing pattern or second breathing pattern correspond with increases in volume until the diaphragm expansion percentage reaches a third threshold and then corresponds with decreases in volume until the diaphragm expansion percentage reaches a fourth threshold.

Clause 50: The base computing device of clause 45, wherein the audio output device comprises a one or more wirelessly connected speakers or wirelessly connected headphones.

Clause 51: A system for dynamically guiding heart rate variability biofeedback, the system comprising: a remote computing device comprising a heart rate sensor, a haptic feedback device, and a first transceiver; a base computing device comprising: an audio output device; a display; a second transceiver; one or more processors; and a memory having stored thereon computer program code that, when executed by the one or more processors, is configured to cause the one or more processors to: receive, from the heart rate sensor via a wireless connection between the first transceiver and the second transceiver, interbeat interval data from the heart rate sensor, wherein the interbeat interval data comprises one or more interbeat intervals; responsive to receiving the interbeat interval data or user input, output an audio pattern associated with a default breathing pattern on the audio output device; dynamically extract one or more characteristics from the interbeat interval data; cause the display to indicate a heart rate variability pattern based on the one or more characteristics; dynamically determine a second breathing pattern based on the one or more characteristics; and dynamically change the audio pattern based on the second breathing pattern.

Clause 52: The system of clause 51, wherein the audio pattern comprises voice guidance or a series of ascending and descending tones.

Clause 53: The system of clause 52, wherein the default breathing pattern and the second breathing pattern corresponds to different inhale-exhale progress curves plotting diaphragm expansion percentage against time.

Clause 54: The system of clause 53, wherein the computer program code is further configured to cause the one or more processors to trigger a change in volume of the audio content associated with the default breathing pattern or second breathing pattern in response to determining the diaphragm expansion percentage changed by a threshold diaphragm expansion percentage.

Clause 55: The system of clause 53, wherein the change in volume during an inhale portion of the default breathing pattern or the second breathing pattern correspond with increases in volume until the diaphragm expansion percentage reaches a first threshold and then corresponds with decreases in volume until the diaphragm expansion percentage reaches a second threshold.

Clause 56: The system of clause 53, wherein the change in volume during an exhale portion of the default breathing pattern or second breathing pattern correspond with increases in volume until the diaphragm expansion percentage reaches a third threshold and then corresponds with decreases in volume until the diaphragm expansion percentage reaches a fourth threshold.

Clause 57: The system of clause 51, wherein: the remote computing device comprises a strain gauge configured to measure blood pressure when a user holds the remote computing device with a first grip and releases to a second grip, and the computer program code is further configured to cause the one or more processors of the base computing device to receive blood pressure data from the remote computing device and update the default breathing pattern or second breathing pattern based on the blood pressure data.

Clause 58: A system for dynamically guiding heart rate variability feedback, the system comprising: a remote computing device comprising a heart rate sensor; a base computing device comprising: a display; one or more processors; and a memory having stored thereon computer program code that, when executed by the one or more processors, is configured to cause the one or more processors to: dynamically receive interbeat interval data from the heart rate sensor, wherein the interbeat interval data comprises one or more interbeat intervals; responsive to receiving user input via the remote computing device, output a display pattern associated with a default breathing pattern via the display; dynamically extract one or more characteristics from the interbeat interval data; dynamically determine a second breathing pattern based on the one or more characteristics; and dynamically change the display pattern based on the second breathing pattern.

Clause 59: The system of clause 58, wherein the second breathing pattern is dynamic and the display comprises a plurality of lights configured to turn in series starting from a lowest positioned light of the plurality of lights according to the second breathing pattern.

Clause 60: The system of clause 58 or 59, wherein the computer program code is further configured to cause the one or more processors to: determine maximum and minimum interbeat interval values; determine whether a threshold number of the maximum and minimum interbeat interval values correspond to a first frequency band; responsive to determining that the threshold number of the maximum and minimum interbeat interval values are in the first frequency band, indicate that the threshold number of interbeat intervals are in the first frequency band via an audio change, display change, haptic change, or a combination thereof.

Clause 61: The system of clause 58, wherein the display pattern comprises a first color and wherein the computer program code is further configured to cause the one or more processors to: determine maximum and minimum interbeat interval values; determine whether a threshold number of the maximum and minimum interbeat interval values correspond to a first frequency band; responsive to determining that the threshold number of the maximum and minimum interbeat interval values are in the first frequency band, display the display pattern in a second color different from the first color.

Clause 62: The system of any of clauses 58 to 61, wherein the computer program code is further configured to cause the one or more processors to: cause at least a portion of the display to display an instantaneous heart rate.

Clause 63: The system of any of clauses 58 to 62, wherein the one or more characteristics comprise a heart rate, a heart rate change, peak-trough amplitude, and peak-trough frequencies, or combinations thereof.

Clause 64: The system of any of clauses 58 to 63, wherein the remote computing device comprises a haptic feedback device configured to provide a haptic feedback pattern corresponding to the interbeat interval or corresponding to the display pattern.

Clause 65: The system of any of clauses 58 to 63, wherein the remote computing device further comprises one or more physiological sensors and the one or more processors of the base computing device are further configured to: receive physiological data from the one or more physiological sensors; determine that the physiological data are within one or more thresholds; map the physiological data to corresponding feedback; and output the feedback via speakers, display, haptic generator, or combinations thereof.

Clause 66: A computing device, comprising: a heart rate sensor; an audio output component; a transceiver; one or more processors; and a memory having stored thereon computer program code that, when executed by the one or more processors, is configured to cause the one or more processors to: output, via the audio output component, an audio content associated with a default breathing pattern via the audio output device; dynamically receive interbeat interval data from the heart rate sensor; dynamically extract one or more characteristics from the interbeat interval data; dynamically determine a second breathing pattern based on the one or more characteristics; and output, via the audio output component, a second audio content associated with the second breathing pattern.

Clause 67: The computing device of clause 66, wherein the computer program code is further configured to cause the one or more processors to: determine maximum and minimum interbeat interval values from the interbeat interval data; determine whether a threshold number of maximum and minimum interbeat interval values correspond to a first frequency band; responsive to determining that the threshold number of maximum and minimum interbeat interval values are in the first frequency band, indicate that the threshold number of maximum and minimum interbeat interval values are in the first frequency band via an audio output indication.

Clause 68: The computing device of clause 66, wherein the computing device comprises a smart phone, smart glasses, smart watch, or headphones.

Clause 69: A system for dynamically guiding a user with heart rate variability feedback, the system comprising: a first computing device comprising: an audio output device; and a display; a second computing device comprising: a heart rate sensor; one or more processors; and memory having stored thereon computer program code that, when executed by the one or more processors, is configured to cause the one or more processors to: receive user input; responsive to receiving the user input, cause the audio output device to output an audio content associated with a default breathing pattern; dynamically receive interbeat interval data from the heart rate sensor; dynamically extract one or more characteristics from the interbeat interval data; cause the display to indicate a dynamic visual pattern based on the one or more characteristics; dynamically determine a second breathing pattern based on the one or more characteristics; and dynamically cause the audio content to change based on the second breathing pattern.

Clause 70: The system of clause 69, wherein the computer program code is further configured to cause the one or more processors to: determine maximum and minimum interbeat interval values from the interbeat interval data; determine whether a threshold number of maximum and minimum interbeat interval values correspond to a first frequency band; and responsive to determining that the threshold number of maximum and minimum interbeat interval values are in the first frequency band, indicate that the threshold number of maximum and minimum interbeat interval values are in the first frequency band via an audio change, a display change, a visual change, a haptic feedback change, or a combination thereof.

Clause 71: The system of clause 69, wherein the dynamic visual pattern is displayed in a first color.

Clause 72: The system of clause 71, wherein the computer program code is further configured to cause the one or more processors to: determine whether a threshold number of interbeat intervals corresponds to a first frequency band; and responsive to determining that the threshold number of interbeat intervals corresponds to the first frequency band, display the dynamic visual pattern in a second color that is different from the first color.

Clause 73: The system of clause 69, wherein the computer program code is further configured to cause the one or more processors to: cause a portion of the display to display an instantaneous heart rate.

Clause 74: The system of clause 69, wherein the one or more characteristics comprise a heart rate, a heart rate change, peak-trough amplitude, and peak-trough frequencies, or combinations thereof.

Clause 75: The system of clause 74, wherein the dynamic visual pattern changes based on characteristics of peak-trough frequencies.

Clause 76: The system of clause 74, wherein the second computing device comprises a haptic feedback device configured to provide a haptic feedback pattern corresponding to the interbeat interval or corresponding to the audio content or the dynamic visual pattern.

Clause 77: The system of clause 74, wherein the second computing device further comprises a haptic feedback device configured to: generate a haptic feedback pattern corresponding to the default breathing pattern or the second breathing pattern which correspond to different inhale-exhale progress curves plotting diaphragm expansion percentage against time; and cause the haptic feedback device to change haptic feedback intensity associated with the default breathing pattern or second breathing pattern in response determining the diaphragm expansion percentage changes by a threshold diaphragm expansion percentage.

Clause 78: The system of clause 77, wherein the change in haptic feedback intensity during an inhale portion of the default breathing pattern or the second breathing pattern correspond with increases in intensity until the diaphragm expansion percentage reaches a first threshold.

Clause 79: The system of clause 77, wherein the change in haptic feedback intensity during an exhale portion of the default breathing pattern or second breathing pattern correspond with increases in intensity until the diaphragm expansion percentage reaches a second threshold.

Clause 80: The system of clause 69, wherein the default breathing pattern and the second breathing pattern corresponds to different inhale-exhale progress curves plotting diaphragm expansion percentage against time, and wherein the computer program code is further configured to cause the one or more processors to trigger a change in volume of the audio output associated with the default breathing pattern or second breathing pattern in response to determining that the diaphragm expansion percentage changed by a threshold diaphragm expansion percentage.

Clause 81: The system of clause 80, wherein the change in volume of the audio output during an inhale portion of the default breathing pattern or the second breathing pattern correspond with increases in volume until the diaphragm expansion percentage reaches a first threshold and then corresponds with decreases in volume until the diaphragm expansion percentage reaches a second threshold.

Clause 82: The system of clause 80, wherein the volume change during an exhale portion of the default breathing pattern or second breathing pattern correspond with increases in volume until the diaphragm expansion percentage reaches a third threshold and then corresponds with decreases in volume until the diaphragm expansion percentage reaches a fourth threshold.

Clause 83: The system of clause 69, wherein: the first computing device comprises a strain gauge configured to measure blood pressure when a user holds the first computing device with a first grip releasing to a second grip, and the computer program code is further configured to cause the one or more processors of the second computing device to receive blood pressure data from the first computing device and update the default breathing pattern or second breathing pattern based on the blood pressure data.

Clause 84: A computing device, comprising: one or more processors; and a memory having stored thereon computer program code that, when executed by the one or more processors, is configured to cause the one or more processors to: dynamically receive interbeat interval data from an instantaneous heart rate sensor, wherein the interbeat interval data comprises one or more interbeat intervals; cause an audio output device to output an audio content associated with a default breathing pattern; dynamically extract one or more characteristics from the interbeat interval data in real time; dynamically determine a second breathing pattern based on the one or more characteristics; and cause the audio content to dynamically change based on the second breathing pattern.

Clause 85: The computing device of clause 84, wherein the default breathing pattern and the second breathing pattern corresponds to different inhale-exhale progress curves plotting diaphragm expansion percentage against time, and wherein the computer program code is further configured to cause the one or more processors to trigger a change in volume of the audio content associated with the default breathing pattern or second breathing pattern in response to determining the diaphragm expansion percentage changed by a threshold diaphragm expansion percentage.

Clause 86: The computing device of clause 85, wherein the computer program code is further configured to cause the one or more processors to trigger a change in volume of the audio content associated with the default breathing pattern or second breathing pattern in response to determining the diaphragm expansion percentage changed by a threshold diaphragm expansion percentage.

Clause 87: The computing device of clause 86, wherein the change in volume during an inhale portion of the default breathing pattern or the second breathing pattern correspond with increases in volume until the diaphragm expansion percentage reaches a first threshold and then corresponds with decreases in volume until the diaphragm expansion percentage reaches a second threshold.

Clause 88: The computing device of clause 87, wherein the change in volume during an exhale portion of the default breathing pattern or second breathing pattern correspond with increases in volume until the diaphragm expansion percentage reaches a third threshold and then corresponds with decreases in volume until the diaphragm expansion percentage reaches a fourth threshold.

Clause 89: The computing device of clause 84, wherein the computer program code is further configured to cause the one or more processors to: cause a display to dynamically indicate a heart rate variability pattern based on the one or more characteristics.

Clause 90: The computing device of clause 85, wherein the computer program code is further configured to cause the one or more processors to: determine whether a threshold number of the one or more interbeat intervals corresponds to a first frequency band; and responsive to determining that the threshold number of interbeat intervals corresponds to the first frequency band, indicate that the threshold number of interbeat intervals are in the first frequency band via an audio change, display change, or both.

Clause 91: The computing device of clause 89, wherein a heart rate variability pattern is displayed in a first color.

Clause 92: The computing device of clause 91, wherein the computer program code is further configured to cause the one or more processors to: determine whether a threshold number of interbeat intervals are in a first frequency band; and responsive to determining that the threshold number of interbeat intervals are in the first frequency band, display the heart rate variability pattern in a second color that is different from the first color.

Clause 93: The computing device of clause 84, wherein the computer program code is further configured to cause the one or more processors to: cause a display to display an instantaneous heart rate.

Clause 94: The computing device of clause 84, wherein the one or more characteristics comprise frequencies associated with heart rate change.

Clause 95: The computing device of clause 89, wherein the indication of the heart rate variability pattern dynamically changes based on the frequencies associated with the heart rate change.

Clause 96: The computing device of clause 84, wherein the audio content comprises a series of ascending and descending tones, tones of different volume levels, or both.

Clause 97: A system comprising: a first computing device comprising: a display; and an audio output device: a second computing device comprising: an instantaneous heart rate sensor; one or more processors; and a memory having stored thereon computer program code that, when executed by the one or more processors, is configured to cause the one or more processors to: dynamically receive interbeat interval data from the instantaneous heart rate sensor, wherein the interbeat interval data comprises one or more interbeat intervals; dynamically extract one or more characteristics from the interbeat interval data; and cause the display to indicate a dynamic heart rate variability pattern based on the one or more characteristics.

Clause 98: The system of clause 97, wherein: the display comprises a plurality of lights and the one or more charac-teristics comprising a heart rate, a heart rate change, peak-trough amplitudes, peak-trough frequencies, or combinations thereof, and indicating the dynamic heart rate variability pattern comprises turning on the plurality of lights in series starting from a lowest positioned light of the plurality of lights, and the dynamic heart rate variability pattern comprises turning off the plurality of lights in series starting from a highest positioned light that is turned on of the plurality of lights.

The features and other aspects and principles of the disclosed embodiments may be implemented in various environments. Such environments and related applications may be specifically constructed for performing the various processes and operations of the disclosed embodiments or they may include a general-purpose computer or computing platform selectively activated or reconfigured by program code to provide the necessary functionality. Further, the processes disclosed herein may be implemented by a suitable combination of hardware, software, and/or firmware. For example, the disclosed embodiments may implement general purpose machines configured to execute software programs that perform processes consistent with the disclosed embodiments. Alternatively, the disclosed embodiments may implement a specialized apparatus or system configured to execute software programs that perform processes consistent with the disclosed embodiments. Furthermore, although some disclosed embodiments may be implemented by general purpose machines as computer processing instructions, all or a portion of the functionality of the disclosed embodiments may be implemented instead in dedicated electronics hardware.

The disclosed embodiments also relate to tangible and non-transitory computer readable media that include program instructions or program code that, when executed by one or more processors, perform one or more computer-implemented operations. The program instructions or program code may include specially designed and constructed instructions or code, and/or instructions and code well-known and available to those having ordinary skill in the computer software arts. For example, the disclosed embodiments may execute high level and/or low-level software instructions, such as machine code (e.g., such as that produced by a compiler) and/or high-level code that can be executed by a processor using an interpreter.

The technology disclosed herein typically involves a high-level design effort to construct a computational system that can appropriately process unpredictable data. Mathematical algorithms may be used as building blocks for a framework, however certain implementations of the system may autonomously learn their own operation parameters, achieving better results, higher accuracy, fewer errors, fewer crashes, and greater speed.

As used in this application, the terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Certain embodiments and implementations of the disclosed technology are described above with reference to block and flow diagrams of systems and methods and/or computer program products according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks.

As an example, embodiments or implementations of the disclosed technology may provide for a computer program product, including a computer-usable medium having a computer-readable program code or program instructions embodied therein, said computer-readable program code adapted to be executed to implement one or more functions specified in the flow diagram block or blocks. Likewise, the computer program instructions may be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

Certain implementations of the disclosed technology described above with reference to user devices may include mobile computing devices. Those skilled in the art recognize that there are several categories of mobile devices, generally known as portable computing devices that can run on batteries but are not usually classified as laptops. For example, mobile devices can include, but are not limited to portable computers, tablet PCs, internet tablets, PDAs, ultra-mobile PCs (UMPCs), wearable devices, and smart phones. Additionally, implementations of the disclosed technology can be utilized with internet of things (IoT) devices, smart televisions and media devices, appliances, automobiles, toys, and voice command devices, along with peripherals that interface with these devices.

In this description, numerous specific details have been set forth. It is to be understood, however, that implementations of the disclosed technology may be practiced without these specific details. In other instances, well-known methods, structures, and techniques have not been shown in detail in order not to obscure an understanding of this description. References to "one embodiment," "an embodiment," "some embodiments," "example embodiment," "various embodiments," "one implementation," "an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may.

As shown throughout the drawings, some features have dash outlines to indicate that the feature is optional and not a required component of a claim unless expressly recited. Even features that are shown in solid lines should not be read into a claim unless expressly recited therein.

Throughout the specification and the claims, the following terms take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. The term "or" is intended to mean an inclusive "or." Further, the terms "a," "an," and "the" are intended to mean one or more unless specified otherwise or clear from the context to be directed to a singular form. By "comprising" or "containing" or "including" is meant that at least the named element, or method step is present in article or method, but does not exclude the presence of other elements or method steps, even if the other such elements or method steps have the same function as what is named.

It is to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Although embodiments are described herein with respect to systems or methods, it is contemplated that embodiments with identical or substantially similar features may alternatively be implemented as systems, methods and/or non-transitory computer-readable media.

As used herein, unless otherwise specified, the use of the ordinal adjectives "first," "second," "third," etc., to describe a common object, merely indicates that different instances of like objects are being referred to, and is not intended to imply that the objects so described must be in a given sequence, either temporally, spatially, in ranking, or in any other manner.

While certain embodiments of this disclosure have been described in connection with what is presently considered to be the most practical and various embodiments, it is to be understood that this disclosure is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the technology and also to enable any person skilled in the art to practice certain embodiments of this technology, including making and using any apparatuses or systems and performing any incorporated methods. The patentable scope of certain embodiments of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for dynamically guiding a user with heart rate variability feedback to a resonance state, the system comprising:
   a first computing device comprising:
      a first transceiver,
      an audio output device; and
      a display;
   a second computing device comprising:
      a second transceiver configured to wirelessly communicate with the first transceiver;
      a heart rate sensor;
      one or more processors; and
      memory having stored thereon computer program code that, when executed by the one or more processors, is configured to cause the one or more processors to:
         receive user input;
         responsive to receiving the user input, cause, via a wireless connection between the second transceiver and the first transceiver, the audio output device to output an audio content associated with a default breathing pattern;
         dynamically receive interbeat interval data from the heart rate sensor;
         dynamically extract one or more characteristics from the interbeat interval data, the one or more characteristics comprising minimum interbeat interval values and maximum interbeat interval values;
         cause, via a wireless connection between the second transceiver and the first transceiver, the display to indicate a dynamic visual pattern based on the one or more characteristics;
         dynamically determine a second breathing pattern by:
            determining a plurality of wave segments based on the minimum interbeat interval values and the maximum interbeat interval values;
            associating the plurality of wave segments with at least partial breathing cycle time segments; and
            determining at least partial breathing cycle times for the second breathing pattern based on calculating weighted averages of the at least partial breathing cycle time segments;
         dynamically cause, via a wireless connection between the second transceiver and the first transceiver, the audio content to change based on the second breathing pattern;
         dynamically determining whether a threshold number of the maximum interbeat interval values and the minimum interbeat interval values are in a first frequency band; and
         responsive to determining that the threshold number of the maximum interbeat interval values and the minimum interbeat interval values are in the first frequency band, cause the first computing device, the second computing device, or both to indicate that the user has entered the resonance state via an audio change, a visual change, a haptic feedback change, or a combination thereof to increase a vagal tone of the user.

2. The system of claim 1, wherein the dynamic visual pattern is displayed in a first color, and wherein the computer program code is further configured to cause the one or more processors to:
   determine whether a threshold number of interbeat intervals corresponds to the first frequency band; and
   responsive to determining that the threshold number of interbeat intervals corresponds to the first frequency band, display the dynamic visual pattern in a second color that is different from the first color.

3. The system of claim 1, wherein the computer program code is further configured to cause the one or more processors to:
   cause a portion of the display to display an instantaneous heart rate.

4. The system of claim 1, wherein the one or more characteristics comprise a heart rate, a heart rate change, peak-trough amplitude, and peak-trough frequencies, or combinations thereof.

5. The system of claim 4, wherein the dynamic visual pattern changes based on characteristics of peak-trough frequencies.

6. The system of claim 4, wherein the second computing device comprises a haptic feedback device configured to provide a haptic feedback pattern corresponding to the interbeat interval or corresponding to the audio content or the dynamic visual pattern.

7. The system of claim 4, wherein the second computing device further comprises a haptic feedback device configured to:
   generate a haptic feedback pattern corresponding to the default breathing pattern or the second breathing pattern which correspond to different inhale-exhale progress curves plotting diaphragm expansion percentage against time; and
   cause the haptic feedback device to change haptic feedback intensity associated with the default breathing pattern or second breathing pattern in response to determining the diaphragm expansion percentage changes by a threshold diaphragm expansion percentage.

8. The system of claim 7, wherein the change in haptic feedback intensity during an inhale portion of the default breathing pattern or the second breathing pattern correspond with increases in intensity until the diaphragm expansion percentage reaches a first threshold.

9. The system of claim 7, wherein the change in haptic feedback intensity during an exhale portion of the default breathing pattern or second breathing pattern correspond with increases in intensity until the diaphragm expansion percentage reaches a second threshold.

10. The system of claim 1, wherein the default breathing pattern and the second breathing pattern corresponds to different inhale-exhale progress curves plotting diaphragm expansion percentage against time, and wherein the computer program code is further configured to cause the one or more processors to trigger a change in volume of the audio output associated with the default breathing pattern or second breathing pattern in response to determining that the diaphragm expansion percentage changed by a threshold diaphragm expansion percentage.

11. The system of claim 10, wherein the change in volume of the audio output during an inhale portion of the default breathing pattern or the second breathing pattern correspond with increases in volume until the diaphragm expansion percentage reaches a first threshold and then corresponds with decreases in volume until the diaphragm expansion percentage reaches a second threshold.

12. The system of claim 10, wherein the change in volume during an exhale portion of the default breathing pattern or second breathing pattern correspond with increases in volume until the diaphragm expansion percentage reaches a third threshold and then corresponds with decreases in volume until the diaphragm expansion percentage reaches a fourth threshold.

13. The system of claim 1, wherein:
the first computing device comprises a strain gauge configured to measure blood pressure when a user holds the first computing device with a first grip releasing to a second grip, and
the computer program code is further configured to cause the one or more processors of the second computing device to receive blood pressure data from the first computing device and update the default breathing pattern or second breathing pattern based on the blood pressure data.

14. A computing device, comprising:
a transceiver
one or more processors; and
a memory having stored thereon computer program code that, when executed by the one or more processors, is configured to cause the one or more processors to:
dynamically receive, via a wireless connection of the transceiver, interbeat interval data from an instantaneous heart rate sensor, wherein the interbeat interval data comprises one or more interbeat intervals;
cause, via the wireless connection of the transceiver, an audio output device to output an audio content associated with a default breathing pattern;
dynamically extract one or more characteristics from the interbeat interval data in real time, the one or more characteristics comprising minimum interbeat interval values and maximum interbeat interval values;
dynamically determine a second breathing pattern by:
determining a plurality of wave segments measured from the minimum interbeat interval values to the maximum interbeat interval values;
associating the plurality of wave segments with at least partial breathing cycle time segments; and
determining at least partial breathing cycle times for the second breathing pattern based on calculating weighted averages of the at least partial breathing cycle time segments;

cause, via the wireless connection of the transceiver, the audio content to dynamically change based on the second breathing pattern; and
dynamically determining whether a threshold number of the maximum and minimum interbeat interval values are in a first frequency band; and
responsive to determining that the threshold number of the maximum interbeat interval values and the minimum interbeat interval values are in the first frequency band, cause, via the wireless connection of the transceiver, the audio output device to indicate a user has reached a resonance state to improve a vagal tone of the user.

15. The computing device of claim 14, wherein the default breathing pattern and the second breathing pattern corresponds to different inhale-exhale progress curves plotting diaphragm expansion percentage against time, and wherein the computer program code is further configured to cause the one or more processors to trigger a change in volume of the audio content associated with the default breathing pattern or second breathing pattern in response to determining the diaphragm expansion percentage changed by a threshold diaphragm expansion percentage.

16. The computing device of claim 15, wherein the computer program code is further configured to cause the one or more processors to trigger a change in volume of the audio content associated with the default breathing pattern or second breathing pattern in response to determining the diaphragm expansion percentage changed by a threshold diaphragm expansion percentage.

17. The computing device of claim 16, wherein the change in volume during an inhale portion of the default breathing pattern or the second breathing pattern correspond with increases in volume until the diaphragm expansion percentage reaches a first threshold and then corresponds with decreases in volume until the diaphragm expansion percentage reaches a second threshold.

18. The computing device of claim 17, wherein the change in volume during an exhale portion of the default breathing pattern or second breathing pattern correspond with increases in volume until the diaphragm expansion percentage reaches a third threshold and then corresponds with decreases in volume until the diaphragm expansion percentage reaches a fourth threshold.

19. The computing device of claim 14, wherein the computer program code is further configured to cause the one or more processors to:
cause a display to dynamically indicate a heart rate variability pattern based on the one or more characteristics.

20. The computing device of claim 15, wherein the computer program code is further configured to cause the one or more processors to:
determine whether a threshold number of the one or more interbeat intervals corresponds to a first frequency band; and
responsive to determining that the threshold number of interbeat intervals corresponds to the first frequency band, indicate that the threshold number of interbeat intervals are in the first frequency band via an audio change, display change, or both.

21. The computing device of claim 19, wherein a heart rate variability pattern is displayed in a first color.

22. The computing device of claim 21, wherein the computer program code is further configured to cause the one or more processors to:

determine whether a threshold number of interbeat intervals are in a first frequency band; and responsive to determining that the threshold number of interbeat intervals are in the first frequency band, display the heart rate variability pattern in a second color that is different from the first color.

23. The computing device of claim 14, wherein the computer program code is further configured to cause the one or more processors to:

cause a display to display an instantaneous heart rate.

24. The computing device of claim 14, wherein the one or more characteristics comprise frequencies associated with heart rate change.

25. The computing device of claim 19, wherein the indication of the heart rate variability pattern dynamically changes based on frequencies associated with a heart rate change.

26. The computing device of claim 14, wherein the audio content comprises a series of ascending and descending tones, tones of different volume levels, or both.

27. A system comprising:

a first computing device comprising:

a display;

a first transceiver; and an audio output device;

a second computing device comprising:

an instantaneous heart rate sensor;

a second transceiver;

one or more processors; and a memory having stored thereon computer program code that, when executed by the one or more processors, is configured to cause the one or more processors to:

dynamically receive interbeat interval data from the instantaneous heart rate sensor, wherein the interbeat interval data comprises one or more interbeat intervals;

dynamically extract one or more characteristics from the interbeat interval data, the one or more characteristics comprising minimum interbeat interval values and maximum interbeat interval values;

dynamically determine a second breathing pattern by:

determining a plurality of interbeat interval wave segments measured from the minimum interbeat interval values to the maximum interbeat interval values;

associating the plurality of wave segments with at least partial breathing cycle time segments; and determining at least partial breathing cycle times for the second breathing pattern based on calculating weighted averages of the at least partial breathing cycle time segments;

cause, via a wireless connection between the first and second transceivers, the display to indicate a dynamic heart rate variability pattern based on the one or more characteristics; and dynamically determining whether a threshold number of the maximum interbeat interval values and the minimum interbeat interval values are in a first frequency band; and responsive to determining that the threshold number of the maximum interbeat interval values and the minimum interbeat interval values are in the first frequency band, cause, via the wireless connection between the first and second transceivers, the display to indicate a user has reached a resonance breathing state to improve a vagal tone of the user.

28. The system of claim 27, wherein:

the display comprises a plurality of lights and the one or more characteristics comprising a heart rate, a heart rate change, peak-trough amplitudes, peak-trough frequencies, or combinations thereof, and indicating the dynamic heart rate variability pattern comprises turning on the plurality of lights in series starting from a lowest positioned light of the plurality of lights, and the dynamic heart rate variability pattern comprises turning off the plurality of lights in series starting from a highest positioned light that is turned on of the plurality of lights.

29. The system of claim 1, wherein dynamically determining whether a threshold number of maximum and minimum interbeat interval values are within the first frequency band comprises determining at least 70% of the last 4 to 20 changes between maximum and minimum interbeat interval values are within frequencies of about 2.4 and about 9.5 cycles or half cycles per minute.

30. The system of claim 27, wherein the one or more processors are further configured to determine that a user reached resonance state when once receiving interbeat interval data corresponding to peak-trough heartbeat amplitudes that are 2 to 4 times initial or typical peak-trough heartbeat amplitudes for the user.

* * * * *